（12）United States Patent
Hope et al.

(10) Patent No.: US 6,670,462 B2
(45) Date of Patent: *Dec. 30, 2003

(54) PROTEIN FRAGMENTS FOR USE IN PROTEIN TARGETING

(75) Inventors: Ralph Graham Hope, Glasgow (GB); John McLauchlan, Glasgow (GB)

(73) Assignee: Medical Research Council, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/968,255

(22) Filed: Oct. 1, 2001

(65) Prior Publication Data

US 2003/0077755 A1 Apr. 24, 2003

Related U.S. Application Data

(63) Continuation-in-part of application No. 09/203,649, filed on Dec. 1, 1998, now Pat. No. 6,340,577.
(51) Int. Cl.$^7$ .......... C07H 21/04; C07K 16/00
(52) U.S. Cl. .......... 536/23.4; 536/23.72; 530/388.3; 530/388.22; 530/388.4
(58) Field of Search .......... 536/23.4, 23.72; 530/388.3, 388.22, 388.4

(56) References Cited

U.S. PATENT DOCUMENTS 6,340,577 B1 * 1/2002 Hope et al. .......... 435/69.7

OTHER PUBLICATIONS

G. Barba, et al., "Hepatitis C Virus Core Protein Shows A Cytoplasmic Localization and Associates to Cellular Lipid Storage Droplets," Proc. Natl., Acad. Sci. USA, vol. 94, Feb. 1997, pp. 1200–1205.
D. Moradpour, et al., "Characterization of Cell Lines Allowing Tightly Regulated Expression of Hepatitis C Virus Core Protein," Virology, vol. 222, pp. 51–63. (1996).
A. Sabile, et al., "Hepatitis C Virus Core Protein Binds to Apolipoprotein AII and Its Secretion Is Modulated by Fibrates," Hepatology, vol. 30, No. 4, Oct. 1999, pp. 1064–1076.

* cited by examiner

Primary Examiner—Hankyel T. Park
(74) Attorney, Agent, or Firm—Knobbe, Martens, Olson & Bear, LLP

(57) ABSTRACT

A protein is described. The protein comprises a lipid globule targeting sequence linked to a protein of interest (POI) wherein the targeting sequence comprises a hepatitis C virus (HCV) core protein or fragment or homologue thereof.

16 Claims, 23 Drawing Sheets

Δ155-161

1-124,145-152

1-173

1-169

Δ155-161

*FIG. 4D*   *FIG. 4E*   *FIG. 4F*

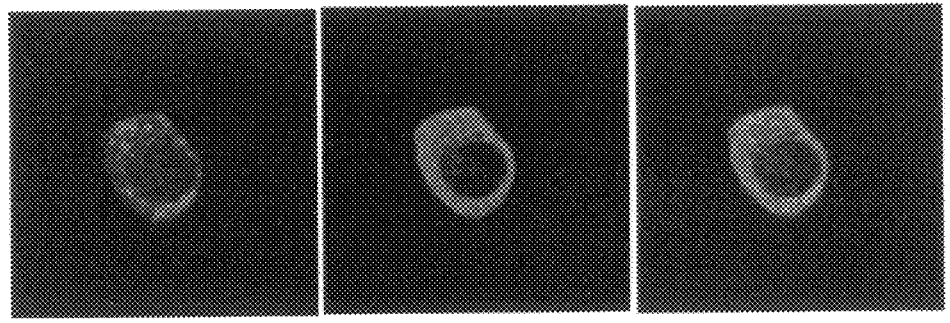
*FIG. 4P*   *FIG. 4Q*   *FIG. 4R*

```
GBV-B  MPVISTQTSPVPAPRTRKNKQTQ-ASYP------------------VSIKTSVERGQRAK 41
           **   *        *   *    *                             *
HCV       MSTNPKPQRKTKRNTNRRPQDVKFPGGGQIVGGVYLLPRRGPRLGVRATRKTSERSQ 57

GBV-B  RKVQRDARPRNYKIAG-------------IHDGLQTLAQAALPAHG---WGRQDPRHKSR 85
           *   *      *                *         *      **  ***  **
HCV    PRGRRQPIPKARRPKGRNWAQPGYPWPLYGNEGCGWAGWLLSPSGSRPSWGPNDPRRRSR 117

GBV-B  NLGILLDYPLGWIGDVTTHTPLVGPLVAGAVVRPVCQIVRLLEDGVNWATGWFG---VHL 142
       ***   *       *     ****    *   *     ** ****** ***
HCV    NLGKVIDTLTCGFVDLMGYIPLVGAPLRG-AARALAHGVRVLEDGVNYATGNLPGCSFSI 176

GBV-B  FVVCLLS-LACPCSG 156
       *   *** *  * *
HCV    FLLALLSCLTVPASA 191
```

Figure 6

PROTEIN FRAGMENTS FOR USE IN PROTEIN TARGETING

CROSS-REFERENCE TO RELATED APPLICATIONS

This application is a Continuation-in-Part application of U.S. patent application Ser. No. 09/203,649, filed Dec. 1, 1998 now U.S. Pat. No. 6,340,577 and, which claims priority under 35 U.S.C. §119 to Great Britain patent application No. 9825953.4, filed Nov. 26, 1998.

FIELD OF THE INVENTION

This invention relates to the use of polypeptides derivable from the core protein of the hepatitis C virus for targeting proteins of interest to lipid globules, in particular lipid globules subsequently secreted into animal milk. The resulting protein/lipid complexes may be used in therapy including the production of vaccines.

BACKGROUND OF THE INVENTION

Hepatitis C virus (HCV) is a major causative agent of chronic hepatitis and liver disease. It is estimated that, worldwide, approximately 300 million individuals are infected with the virus, 20% of whom are likely to develop mild to severe liver disease or carcinoma. Apart from the risk of succumbing to the long term effects of infection, these individuals also represent a large reservoir of virus for future transmissions. To date, the only widely used therapy for HCV is treatment with interferon. However, sustained response is achieved in only about 20% of cases. Moreover, no vaccine currently exists to protect against infection. Since growth of the virus has not been possible to date in tissue culture systems, very little is known also about the molecular events which occur during viral replication.

The core protein of HCV is predicted to constitute the capsid of virus particles. From various studies, expression of this protein results in a range of effects on intracellular processes, including a decrease in transcription of genes from HBV and HIV and alterations to apoptosis. There is also evidence from a study on transgenic mice that liver-specific expression of core may be linked to the development of steatosis (fatty liver), a condition commonly found in HCV-infected individuals which is characterized by the accumulation of fat deposits within hepatocytes. Thus, core protein may also influence lipid metabolism within the liver. Other results from studies on human sera suggest that HCV virus particles are found associated with lipoprotein particles which are produced by the liver. It has also been shown that HCV core protein associates with lipid droplets within cells (Barba, G. et al., 1997; Moradpour, D. et al., 1996). The droplets are storage compartments for both triacylglycerols and cholesterol esters which can be used as substrates for oxidation in mitochondria and for the formation of membranes. In specialized cells, stored cholesterol is used for steroid hormone synthesis.

Within the liver, lipid droplets also function as a site for storage of precursors of the lipid which is secreted from this organ in the form of lipoprotein particles. Although lipid droplets were identified several decades ago and they can be readily detected by staining methods, very little is known about the processes of assembly, storage and disassembly within the cell. One protein, termed adipocyte-related differentiation protein (ADRP), has been found to associate with lipid droplets in a range of cell types and in certain organs. To date, it is the only protein which is apparently not cell-type specific that has this intracellular distribution. It is proposed that ADRP may be required for maintenance of lipid droplets within cells, however the precise function of the protein has not been identified.

SUMMARY OF THE INVENTION

Particular sequences within the hepatitis C virus core protein that direct association of HCV core protein with intracellular lipid globules have now been characterized. These sequences can thus be used to target other proteins to lipid globules, including lipid globules secreted by milk-producing cells. We have also shown that expression of core protein and its resultant association with lipid droplets results in loss of ADRP from the droplets. Furthermore, progressive increases in core expression result in diminishing amounts of ADRP to undetectable levels. Since it has been shown previously that ADRP is also secreted as a component of fat globules in milk from humans, cows and rats, proteins comprising HCV core protein sequences may also be secreted into animal milk. Thus fusion proteins comprising HCV core protein elements fused to proteins of interest may be targeted specifically to lipid globules secreted into the milk produced by a variety of animals and the proteins extracted from the milk. This will facilitate the expression and secretion into milk of proteins of interest and provide an effective method of producing recombinant proteins in transgenic animals.

Accordingly, the present invention provides a protein comprising a lipid globule targeting sequence linked to a protein of interest (POI) wherein the targeting sequence comprises a hepatitis C virus (HCV) core protein or fragment or homologue thereof. Preferably, the lipid globule targeting sequence comprises amino acids from 125 to 144 and/or 161 to 166 of the HCV core protein as set out in SEQ ID. Nos. 2 and 3, or the equivalent amino acids in other HCV strains/isolates. More preferably, the lipid globule targeting sequence also comprises a hydrophilic amino acid sequence of at least 8 amino acids. The present invention also provides an isolated polypeptide consisting essentially of a lipid globule targeting sequence wherein the targeting sequence comprises from amino acids 125 to 144 and 161 to 166 of an HCV core protein linked to a hydrophilic amino acid sequence of at least 8 amino acids.

The protein of interest is preferably a protein expressed by a pathogen, preferably a viral or bacterial protein or fragment thereof, more preferably comprising at least one epitope.

In another aspect, the present invention provides a polynucleotide encoding a protein of the invention. The present invention also provides a polynucleotide encoding a protein of the invention operably linked to a control sequence permitting expression of the protein in a suitable host cell. Preferred host cells include adipocytes and milk-secreting cells.

The invention further provides a nucleic acid vector comprising a polynucleotide of the invention. The invention also provides a host cell comprising a polynucleotide of the invention or a nucleic acid vector of the invention.

In another aspect, the present invention provides a method for producing a protein of the invention which method comprises culturing a host cell of the invention under conditions which allow expression of the protein, and recovering the protein.

The proteins of the invention may advantageously be extracted from cells associated with the lipid globules to which the proteins have been directed by the lipid globule targeting sequence. In particular, proteins produced in milk-secreting cells in milk-producing animals may conveniently be extracted from the animal's milk. These protein/lipid complexes may be used without further purification. Indeed, lipids have been used as adjuvants in the preparation of vaccine compositions. Consequently, protein/lipid globule compositions of the invention may be used in the preparation of vaccines, in particular where the protein of interest is immunogenic.

Thus, the invention also provides a composition comprising a protein of the invention and a lipid globule. Preferably the lipid globule is a constituent of mammalian milk.

The compositions, proteins, polynucleotides and vectors of the present invention may be used in the prevention or treatment of pathogenic infections. Thus, in a further aspect, the present invention provides a vaccine composition comprising a composition, protein, polynucleotide or vector of the invention together with a pharmaceutically acceptable carrier or diluent. It may be preferred to use the proteins of the invention in combination with the active constituents of other vaccine compositions to increase their effectiveness.

The present invention also provides a method of treating or preventing a pathogenic infection in a human or animal which comprises administering to the human or animal an amount of a composition, protein, polynucleotide or vector of the invention sufficient to achieve a beneficial immunological effect.

DETAILED DESCRIPTION OF THE PREFERRED EMBODIMENT

Although in general the techniques mentioned herein are well known in the art, reference may be made in particular to Sambrook et al., Molecular Cloning, A Laboratory Manual (1989) and Ausubel et al., Current Protocols in Molecular Biology (1995), John Wiley & Sons, Inc.

A. Proteins/Polypeptides

The term "protein" includes single-chain polypeptide molecules as well as multiple-polypeptide complexes where individual constituent polypeptides are linked by covalent or non-covalent means. The term "polypeptide" includes peptides of two or more amino acids in length, typically having more than 5, 10 or 20 amino acids. Proteins of the invention generally comprise at least two components—a lipid globule targeting sequence which is capable of targeting molecules to lipid globules and a molecule of interest, typically a protein.

1. Lipid Globule Targeting Sequences

The term "lipid globule targeting sequence" means an amino acid sequence which is capable of association with a lipid globule, preferably a biologically occurring lipid globule such as an intracellular lipid globule as found in adipocytes or a secreted lipid globule as found in mammalian milk. In addition, the lipid globule targeting sequence is preferably capable of association with a lipid globule when linked to a protein of interest such that the protein of interest is also associated with the lipid globule by virtue of being linked to the targeting sequence. Lipid globule association may take place within a non-cellular and/or extra-cellular environment, such as in an apparatus—for example a tube or vat. Alternatively, it may take place in a cellular environment where the expressed targeting sequence is directed to intracellular lipid droplets or the membranes of such droplets. It is especially preferred that the targeting sequence is directed to lipid droplets which are subsequently secreted into the extracellular environment, for example during the production by female animals of milk.

The ability of an amino acid sequence to associate with/target lipid globules can be assessed either in vitro or in vivo. For example, a candidate targeting sequence may be added to a dispersion of lipid globules (such as a mixture of phospholipid and triacylglycerol) in an aqueous solvent, the mixture sonicated and the degree of partition between aqueous and lipid phases determined by fractionation. Typically fractionation of the mixture would involve increasing the density of the solution with sorbitol or sodium bromide and ultracentrifuging the solution. The lipid complexes migrate to the top of the centrifuge tube and this upper lipid layer is then examined for candidate targeting sequence. Preferably, a suitable lipid globule targeting sequence should partition at least 50:50 lipid:aqueous phase, more preferably at least 75:25, 80:20 or 90:10.

Another suitable test may involve introducing a polynucleotide encoding a candidate sequence, optionally linked to a protein of interest, into a milk-producing cell in culture and determining whether, the targeting sequence/protein of interest has been secreted into the culture medium. The immunocytochemical technique illustrated in the Examples may also be used.

Suitable lipid globule targeting sequences may be obtained from an HCV core protein.

The amino acid sequence of the HCV core protein has been obtained for a large number of different HCV isolates. These sequences are readily available to the skilled person. One such sequence, for HCV strain Glasgow, is set out in SEQ ID No. 1. The means for cloning and identifying new HCV strains, and thus obtaining further core sequences, are described in EP-B-318,216

According to the present invention, it is preferred to use fragments of the HCV core protein which are capable of targeting molecules, to which they are linked, to lipid globules. Amino acid numbering for preferred fragments set out below is with reference to SEQ ID. No. 1. However it will be understood that equivalent fragments of the core protein of other HCV strains/isolates may also be used. An HCV core protein-derivable lipid globule targeting sequence of the invention is preferably a minimal amino acid sequence which can target a molecule, typically a protein, to lipid globules. The minimal sequence will typically comprise a hydrophobic amino acid sequence derived from amino acids 120 to 169 of an HCV core sequence, preferably linked to a hydrophilic amino acid sequence of at least 8, preferably 10, more preferably at least 12 amino acids. It is not necessary for the hydrophilic sequence to be contiguous with the hydrophobic sequence. For example, a protein of interest may be placed between the two sequences such that the hydrophilic sequence is at the N-terminus and the hydrophobic sequence is at the C-terminus.

The hydrophobic amino acid sequence typically comprises at least 10, preferably at least 15 or 20 contiguous amino acids and has a hydropathy index of at least +40 kJ/mol (determined, for example, theoretically as described by Engelman et al., 1986). The hydrophilic amino acid sequence typically has a hydropathy plot of less than −20 kJ/mol, preferably less than −40 kJ/mol.

Preferred HCV core fragments contain amino acids 161 to 166 (SEQ ID. No. 3). It is also preferred to use fragments of the HCV core protein that contain amino acids 125 to 144 (SEQ ID. No. 2). In a preferred embodiment, HCV core protein fragments of the invention contain both amino acids 125 to 144 and amino acids 161 to 166. In an especially preferred embodiment, the lipid targeting sequence of the invention comprises a hydrophilic amino acid sequence containing amino acids 1 to 8 of the HCV core sequence. Other preferred fragments contain amino acids 1 to 173 or 1 to 169.

Since it has also now been shown that amino acids 9 to 43, 49 to 75, 80 to 118 and 155 to 161 are not required for lipid association, preferred HCV core protein fragments of the invention lack one or more of these sequences. In particular, it is preferred that HCV core protein fragments of the invention lack amino acids 9 to 43. Suitable fragments will be at least about 5, e.g. 10, 12, 15 or 20 amino acids in size and preferably have less than 100, 90, 80, 70, 60 or 50 amino acids. In a preferred aspect, fragments contain an HCV epitope.

Lipid globule targeting sequences of the invention, for example HCV core protein sequences and fragments thereof, may, however, be part of a larger polypeptide, for example a fusion protein. In this case, the additional polypeptide sequences are preferably polypeptide sequences with which the lipid globule targeting sequence of the invention is not normally associated.

It will be understood that lipid globule targeting sequences of the invention are not limited to sequences obtained from HCV core protein but also include homologous sequences obtained from any source, for example related viral proteins, cellular homologues and synthetic peptides, as well as variants or derivatives thereof. Thus, the present invention covers variants, homologues or derivatives of the targeting sequences of the present invention, as well as variants, homologues or derivatives of the nucleotide sequence coding for the targeting sequences of the present invention.

In the context of the present invention, a homologous sequence is taken to include an amino acid sequence which is at least 60, 70, 80 or 90% identical, preferably at least 95 or 98% identical at the amino acid level over at least 5, preferably 8, 10, 15, 20, 30 or 40 amino acids with an HCV core protein lipid targeting sequence, for example as shown in the sequence listing herein. In particular, homology should typically be considered with respect to those regions of the targeting sequence known to be essential for lipid globule association rather than non-essential neighboring sequences. Homology comparisons can be conducted by eye, or more usually, with the aid of readily available sequence comparison programs. These commercially available computer programs can calculate % homology between two or more sequences. A typical example of such a computer program is CLUSTAL.

Sequence homology (or identity) may moreover be determined using any suitable homology algorithm, using for example default parameters. Advantageously, the BLAST algorithm is employed, with parameters set to default values. The BLAST algorithm is described in detail at http://www.ncbi.nih.gov/BLAST/blast_help.html, which is incorporated herein by reference. The search parameters are defined as follows, and are advantageously set to the defined default parameters.

Advantageously, "substantial homology" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (see http://www.ncbi.nih.gov/BLAST/blast_help.html) with a few enhancements. The BLAST programs were tailored for sequence similarity searching, for example to identify homologues to a query sequence. The programs are not generally useful for motif-style searching. For a discussion of basic issues in similarity searching of sequence databases, see Altschul et al. (1994).

The five BLAST programs available at http://www.ncbi.nlm.nih.gov perform the following tasks:

blastp—compares an amino acid query sequence against a protein sequence database;

blastn—compares a nucleotide query sequence against a nucleotide sequence database;

blastx—compares the six-frame conceptual translation products of a nucleotide query sequence (both strands) against a protein sequence database;

tblastn—compares a protein query sequence against a nucleotide sequence database dynamically translated in all six reading frames (both strands).

tblastx—compares the six-frame translations of a nucleotide query sequence against the six-frame translations of a nucleotide sequence database.

BLAST uses the following search parameters:

HISTOGRAM—Display a histogram of scores for each search; default is yes. (See parameter H in the BLAST Manual).

DESCRIPTIONS—Restricts the number of short descriptions of matching sequences reported to the number specified; default limit is 100 descriptions. (See parameter V in the manual page). See also EXPECT and CUTOFF.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER Mask off segments of the query sequence that have low compositional complexity, as determined by the SEG program of Wootton & Federhen (1993), or segments consisting of short-periodicity internal repeats, as determined by the XNU program of Claverie & States (1993), or, for BLASTN, by the DUST program of Tatusov and Lipman (see http://www.ncbi.nlm.nih.gov). Filtering can eliminate statistically significant but biologically uninteresting reports from the blast output (e.g. hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi Causes NCBI gi identifiers to be shown in the output, in addition to the accession and/or locus name.

Most preferably, sequence comparisons are conducted using the simple BLAST search algorithm provided at http://www.ncbi.nlm.nih.gov/BLAST.

Other computer program methods to determine identify and similarity between the two sequences include but are not limited to the GCG program package (Devereux et al., 1984) and FASTA (Atschul et al., 1990).

Lipid globule targeting sequences of the invention, for example HCV core protein sequences, variants, homologues and fragments thereof, may be modified for use in the present invention. Typically, modifications are made that maintain the hydrophobicity/hydrophilicity of the sequence Amino acid substitutions may be made, for example from 1, 2 or 3 to 10, 20 or 30 substitutions provided that the modified sequence retains the ability to target molecules to lipid globules. Amino acid substitutions may include the use of non-naturally occurring analogues, for example to increase blood plasma half-life of a therapeutically administered polypeptide.

Conservative substitutions may be made, for example according to the Table below. Amino acids in the same block in the second column and preferably in the same line in the third column may be substituted for each other.

The terms "variant", "homologue" or "derivative" in relation to the targeting sequence of the present invention include any substitution of, variation of, modification of, replacement of, deletion of or addition of one (or more) amino acids from or to the sequence providing the resultant amino acid sequence has a lipid globule targeting activity, preferably having at least the same activity of the targeting sequence presented in the sequence listings.

| ALIPHATIC | Non-polar | GAP |
| | | ILV |
| | Polar - uncharged | CSTM |
| | | NQ |
| | Polar - charged | DE |
| | | KR |
| AROMATIC | | HFWY |

The terms "variant", "homologue" or "derivative" in relation to the targeting sequence of the present invention include any substitution of, variation of, modification of, replacement of, deletion of or addition of one (or more) amino acids from or to the sequence providing the resultant amino acid sequence has a lipid globule targeting activity, preferably having at least the same activity of the targeting sequence presented in the sequence listings.

2. Proteins of Interest

Proteins of interest may include, for example, proteins involved in the regulation of cell division, for example growth factors including neurotrophic growth factors, cytokines (such as α-, β- or γ-interferon, interleukins including IL-1, IL-2, tumor necrosis factor, or insulin-like growth factors I or II), protein kinases (such as MAP kinase), protein phosphatases and cellular receptors for any of the above. The protein may also be an enzyme involved in cellular metabolic pathways, for example enzymes involved in amino acid biosynthesis or degradation (such as tyrosine hydroxylase), purine or pyrimidine biosynthesis or degradation, and the biosynthesis or degradation of neurotransmitters, such as dopamine, or a protein involved in the regulation of such pathways, for example protein kinases and phosphatases. The protein may also be a transcription factors or proteins involved in their regulation, for example pocket proteins of the Rb family such as Rb or p107, membrane proteins, structural proteins or heat shock proteins such as hsp70. Proteins of interest are preferably lipid soluble or contain regions which allow a portion of the protein to be buried in a lipid globule. Preferably the POI will not hinder the lipid targeting effect of the lipid globule targeting sequence.

Preferably, the protein of interest is of therapeutic use, or the function of which may be implicated in a disease process. Proteins of interest may also contain antigenic polypeptides for use as vaccines. Preferably such antigenic polypeptides are derived from pathogenic organisms, for example bacteria or viruses, or from tumors. In particular antigenic polypeptides containing HCV epitopes may be used. Extensive epitope mapping of the HCV genome has already been carried out and the majority of HCV epitopes characterized. Epitopes may be linear or conformational. In the case of HCV core protein epitopes, the HCV core protein targeting sequence of the invention may already contain suitable HCV epitopes and this being the case, it may not be necessary to include further antigenic sequences. Consequently an HCV core protein sequence may be used according to the present invention without being fused to a protein of interest. However, proteins of interest should preferably not be sequences with which the lipid globule targeting sequences are normally associated.

In addition to being linked to the lipid globule targeting sequence, proteins of interest may be linked to further fusion proteins. Polypeptides of the invention may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the HCV core protein sequence and/or between the HCV core protein sequence and the protein of interest to allow removal of fusion protein sequences. Preferably the fusion protein will not hinder the lipid targeting effect of the lipid globule targeting sequence. The targeting sequence may be linked to either the N-terminus or the C-terminus of the fusion protein partners or proteins of interest Proteins of the invention are typically made by recombinant means, for example as described below. However they may also be made by synthetic means using techniques well known to skilled persons such as solid phase synthesis.

Proteins of the invention may be in a substantially isolated form. It will be understood that the protein may be mixed with carriers or diluents which will not interfere with the intended purpose of the protein and still be regarded as substantially isolated. A protein of the invention may also be in a substantially purified form, in which case it will generally comprise the protein in a preparation in which more than 90%, e.g. 95%, 98% or 99% of the protein in the preparation is a protein of the invention.

B. Polynucleotides and Vectors.

Polynucleotides of the invention comprise nucleic acid sequences encoding the lipid globule targeting sequences of the invention and proteins of the invention. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Polynucleotides of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

The terms "variant", "homologue" or "derivative" in relation to the nucleotide sequence coding for the lipid targeting sequence of the present invention include any substitution of, variation of, modification of, replacement of, deletion of or addition of one (or more) nucleic acid from or to the sequence providing the resultant nucleotide sequence codes for a protein having lipid targeting activity, preferably having at least the same activity of the targeting sequence presented in the sequence listings.

As indicated above, with respect to sequence homology, preferably there is at least 75%, more preferably at least 85%, more preferably at least 90% homology to the sequences shown in the sequence listing herein. More preferably there is at least 95%, more preferably at least 98%, homology. Nucleotide homology comparisons may be conducted as described above.

The present invention also encompasses nucleotide sequences that are capable of hybridizing selectively to the sequences presented herein, or any variant, fragment or derivative thereof, or to the complement of any of the above. Nucleotide sequences are preferably at least 15 nucleotides in length, more preferably at least 20, 30, 40 or 50 nucleotides in length.

The term "hybridization" as used herein shall include "the process by which a strand of nucleic acid joins with a complementary strand through base pairing" (Coombs J (1994) Dictionary of Biotechnology, Stockton Press, New York N.Y.) as well as the process of amplification as carried out in polymerase chain reaction technologies as described in Dieffenbach C W and G S Dveksler (1995, PCR Primer, a Laboratory Manual, Cold Spring Harbor Press, Plainview N.Y.).

Polynucleotides of the invention capable of selectively hybridizing to the nucleotide sequences presented herein, or to their complement, will be generally at least 70%, preferably at least 80 or 90% and more preferably at least 95% or 98% homologous to the corresponding nucleotide sequence presented herein over a region of at least 20, preferably at least 25 or 30, for instance at least 40, 60 or 100 or more contiguous nucleotides. Preferred polynucleotides of the invention will comprise regions homologous to nucleotides 715 to 774 and/or nucleotides 826 to 840 of SEQ ID No. 1, preferably at least 80 or 90% and more preferably at least 95% homologous to to nucleotides 715 to 774 and/or nucleotides 826 to 840 of SEQ ID No. 1.

The term "selectively hybridizable" means that the polynucleotide used as a probe is used under conditions where a target polynucleotide of the invention is found to hybridize to the probe at a level significantly above background. The background hybridization may occur because of other polynucleotides present, for example, in the cDNA or genomic DNA library being screened. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}$P.

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm–5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

In a preferred aspect, the present invention covers nucleotide sequences that can hybridize to the nucleotide sequence of the present invention under stringent conditions (e.g. 65° C. and 0.1×SSC {1×SSC=0.15 M NaCl, 0.015 M Na$_3$ citrate pH 7.0).

Where the polynucleotide of the invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Polynucleotides which are not 100% homologous to the sequences of the present invention but fall within the scope of the invention can be obtained in a number of ways. Other HCV core protein variants of the HCV core protein sequence described herein may be obtained for example by probing DNA libraries made from a range of HCV infected individuals, for example individuals from different populations. In addition, other viral, or cellular homologues particularly cellular homologues found in mammalian cells (e.g. rat, mouse, bovine and primate cells), may be obtained and such homologues and fragments thereof in general will be capable of selectively hybridizing to the sequences shown in the sequence listing herein. Such sequences may be obtained by probing cDNA libraries made from or genomic DNA libraries from other animal species, and probing such libraries with probes comprising all or part of SEQ ID. 1 under conditions of medium to high stringency.

Variants and strain/species homologues may also be obtained using degenerate PCR which will use primers designed to target sequences within the variants and homologues encoding conserved amino acid sequences within the lipid globule targeting sequences of the present invention. Conserved sequences can be predicted, for example, by aligning the HCV core protein amino acid sequences from several HCV isolates. Such HCV sequence comparisons are widely available in the art. The primers will contain one or more degenerate positions and will be used at stringency conditions lower than those used for cloning sequences with single sequence primers against known sequences.

Alternatively, such polynucleotides may be obtained by site directed mutagenesis of characterized lipid globule targeting sequences, such as SEQ ID. No 1. This may be useful where for example silent codon changes are required to sequences to optimize codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides of the invention may be used to produce a primer, e.g. a PCR primer, a primer for an alternative amplification reaction, a probe e.g. labeled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as a DNA polynucleotides and probes according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence/POI which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector Polynucleotides of the invention can be incorporated into a recombinant replicable vector. The vector may be used to replicate the nucleic acid in a compatible host cell.

Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

Such vectors may be transformed or transfected into a suitable host cell as described below to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell either in vitro or in vivo.

Control sequences operably linked to sequences encoding the protein of the invention include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

The promoter is typically selected from promoters which are functional in mammalian, cells, although prokaryotic promoters and promoters functional in other eukaryotic cells may be used. The promoter is typically derived from promoter sequences of viral or eukaryotic genes. For example, it may be a promoter derived from the genome of a cell in which expression of the protein is to occur. With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). Tissue-specific promoters specific for adipocyte cells (such as the perilipin promoter), in particular milk-producing cells, are particularly preferred, for example promoters for α-lactalbumin, β-lactoglobulin, whey acidic protein or butyrophilin genes. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the POI can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

C. Host Cells

Vectors and polynucleotides of the invention may be introduced into host cells for the purpose of replicating the vectors/polynucleotides and/or expressing the proteins of the invention encoded by the polynucleotides of the invention. Although the proteins of the invention may be produced using prokaryotic cells as host cells, it is preferred to use eukaryotic cells, for example plant, yeast, insect or mammalian cells, in particular mammalian cells. Particularly preferred cells are those with substantial amounts of intracellular lipid droplets/globules, for example adipocytes. In a preferred embodiment, host cells which secrete lipid globules, for example milk-producing cells, are used. Mammalian cell lines may be transfected in vitro or alternatively, intact multicellular organisms may be used, for example ungulates such as cows, goats, pigs and sheep. Preferably animals with high milk yields are used.

Vectors/polynucleotides of the invention may be introduced into suitable host cells using a variety of techniques known in the art, such as transfection, transformation and electroporation. Where vectors/polynucleotides of the invention are to be administered to animals, several techniques are known in the art, for example infection with recombinant viral vectors such as herpes simplex viruses and adenoviruses, direct injection of nucleic acids and biolistic transformation. Alternatively, transgenic animals may be produced using suitable techniques.

For example, one method used to produce a transgenic animal involves microinjecting a nucleic acid into pronuclear stage eggs by standard methods. Injected eggs are then cultured before transfer into the oviducts of pseudopregnant recipients. Analysis of animals which may contain transgenic sequences would be performed by either PCR or Southern blot analysis following standard methods.

Transgenic animals may also be produced by nuclear transfer technology as described in Schnieke, A. E. et al. (1997) and Cibelli, J. B. et al. (1998). Using this method, fibroblasts from donor animals are stably transfected with a plasmid incorporating the coding sequences for core or any proteins of interest fused to lipid globule targeting sequences under the control of regulatory elements required for optimal expression in mammary cells. Stable transfectants are then fused to enucleated oocytes, cultured and transferred into female recipients.

When constructing suitable nucleic acids of the invention for introduction into mammalian eggs during production of transgenic animals, regulatory sequences typically used are promoter elements that are required for tissue-specific expression, examples of which are listed in Section B. Additionally, regulatory sequences may include introns, enhancer elements and sequences flanking the portion of the coding region which are known to influence expression in transgenic animals and may be required for optimal expression in milk. These regulatory elements may be of natural or synthetic origin and placed upstream of, within and downstream of the coding sequences. The nucleic acid vector used for production of transgenic animals may incorporate also the entire β-lactoglubulin gene. Such methodology is known to increase expression levels in transgenic animals (see for example Sola, I. et al., 1998).

D. Protein Expression and Purification

Host cells comprising polynucleotides of the invention may be used to express proteins of the invention. Host cells may be cultured under suitable conditions which allow expression of the proteins of the invention. Expression of the proteins of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Proteins of the invention can be extracted from host cells by a variety of techniques known in the art, including enzymatic, chemical and/or osmotic lysis and physical disruption. Although a large number of different purification protocols may be used, given the ability of the HCV core proteins of the invention to target proteins of interest to lipid globules, a preferred extraction/purification protocol involves centrifuging cell homogenates at high speed (for example 100, 000 g for 60 mins at 2 to 4° C.) and removing the resulting layer of floating lipids. This will function as a primary purification step. Further purification can then be performed if necessary using, for example, column chromatography such as ion-exchange or affinity chromatography. Cells which secrete lipid globules may also conveniently be used and the lipid globules harvested from the culture supernatant.

Proteins associated with the membrane surrounding fat globules can be fractionated into soluble and insoluble fractions by extraction with 1% (w/v) Triton X-100/1.5 M NaCl/10 mM Tris (pH 7.0), by extraction with 1.5% (w/v) dodecyl β-D maltoside/0.75 M aminohexanoic acid/10 mM Hepes (pH 7.0) or by sequential extraction with these two detergent-containing solutions (Patton, S. and Huston, G. E., 1986, Lipids 21; 170–174). Suspension of the fat globule components in the detergent-containing solution can be achieved by using an all-glass homogenizer, and keeping on ice for 30 to 60 min, after which insoluble and soluble materials can be separated by centrifugation for 60 min at 2° C. and 150,000 g. The above conditions can be modified to analyse whether core protein or a fusion protein containing core as a component is attached to fat globules. Other detergents, both ionic and non-ionic, along with salt solutions at various concentrations could be used to derive the proteinaceous material from fat globules. The incubation times and temperatures may be optimized by empirical means.

A particularly preferred method for producing proteins of the invention involves using milk-producing animals stably transfected with suitable expression vectors, or transgenic milk-producing animals. In these cases, the milk is harvested from the animals, and the lipid globule/protein complex extracted.

Milk fat globules can be separated from whole milk by centrifugation at 2000 g for 15 min at room temperature where they collect as a layer at the top of the centrifuge tube (Freudenstein, C. et al., 1979). Alternatively, sucrose can be added to milk (5% w/v) and this milk solution can be layered below an overlying layer of water, buffer or saline solution. Following centrifugation at 2000 g for 20 min at room temperature, milk fat globules collect as a layer at the top of the centrifuge tube. In both methods, fat globules can be collected by a spoon, pipette or similar device. To enhance purity, the fat globules can be dispersed in a saline solution and collected by centrifugation as described above. These methods are suitable for volumes of less than 1 ml up to approximately 1 liter. For greater volumes, a cream separator could be employed.

E. Compositions

Proteins of the invention may be combined with various components to produce compositions of the invention. These components may include pharmaceutically acceptable carriers or diluents, and/or vaccine components as described below. In particular, a composition of the invention comprises a protein of the invention together with a lipid globule. Since the HCV core protein of the invention targets proteins of interest to lipid globules, one of the products of the purification procedure may be the protein of interest already associated with a lipid globule. Alternatively, proteins of the invention may be produced and/or extracted to provide an aqueous product, substantially free of associated lipids, and lipid globules added to the purified product. Preferred lipid globules are those which occur in mammalian milk.

F. Administration

The compositions of the invention may be administered by direct injection. Preferably the compositions are combined with a pharmaceutically acceptable carrier or diluent to produce a pharmaceutical composition (which may be for human or animal use). Suitable carriers and diluents include isotonic saline solutions, for example phosphate-buffered saline. The composition may be formulated for parenteral, intramuscular, intravenous, subcutaneous, intraocular or transdermal administration. Typically, each protein may be administered at a dose of from 0.01 to 30 mg/kg body weight, preferably from 0.1 to 10 mg/kg, more preferably from 0.1 to 1 mg/kg body weight.

The polynucleotides/vectors of the invention may be administered directly as a naked nucleic acid construct, preferably further comprising flanking sequences homologous to the host cell genome. When the polynucleotides/vectors are administered as a naked nucleic acid, the amount of nucleic acid administered is typically in the range of from 1 $\mu$g to 10 mg, preferably from 100 $\mu$g to 1 mg.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example lipofectam™ and transfectam™). Typically, nucleic acid constructs are mixed with the transfection agent to produce a composition.

Preferably the polynucleotide or vector of the invention is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration.

The routes of administration and dosages described are intended only as a guide since a skilled practitioner will be able to determine readily the optimum route of administration and dosage for any particular patient and condition.

G. Preparation of Vaccines

Vaccines may be prepared from one or more proteins of the invention or compositions of the invention where the proteins are immunogenic, for example comprising epitopes from viral or bacterial pathogens. They may also include one or more additional immunogenic polypeptides known in the art. The preparation of vaccines which contain an immunogenic polypeptide(s) as active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing an antigenic sequence resulting from administration of this polypeptide in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and may contain 10% to 95% of active ingredient, preferably 25% to 70%. Where the vaccine composition is lyophilized, the lyophilized material may be reconstituted prior to administration, e.g. as a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose. These capsules may be used as such, or alternatively, the proteins and compositions of the invention may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

H. Dosage and Administration of Vaccines

The vaccines are administered in a manner compatible with the dosage formulation, and in such amount as will be prophylactically and/or therapeutically effective. The quantity to be administered, which may generally be in the range of 5 mg to 250 mg of antigen per dose, depends on the subject to be treated, capacity of the subject's immune system to synthesize antibodies, and the degree of protection desired. Precise amounts of active ingredient required to be administered may depend on the judgement of the practitioner and may be peculiar to each subject.

The vaccine may be given in a single dose schedule, or preferably in a multiple dose schedule. A multiple dose schedule is one in which a primary course of vaccination may be with 1 to 10 separate doses, followed by other doses given at subsequent time intervals required to maintain and or reinforce the immune response, for example, at 1 to 4 months for a second dose, and if needed, a subsequent dose(s) after several months. The dosage regimen will also, at least in part, be determined by the need of the individual and be dependent upon the judgement of the practitioner.

In addition, the vaccine containing the immunogenic proteins of the invention may be administered in conjunction with other immunoregulatory agents, for example, immunoglobulins.

I. Preparation of Antibodies Against the Polypeptides of the Invention

The immunogenic proteins of the invention prepared as described above can be used to produce antibodies, both polyclonal and monoclonal. If polyclonal antibodies are desired, a selected mammal (e.g., mouse, rabbit, goat, horse, etc.) is immunized with an immunogenic protein of the invention. Serum from the immunized animal is collected and treated according to known procedures. If serum containing polyclonal antibodies to an immunogenic protein of the invention contains antibodies to other antigens, the polyclonal antibodies can be purified by immunoaffinity chromatography. Techniques for producing and processing polyclonal antisera are known in the art.

Monoclonal antibodies directed against epitopes of interest in the proteins of the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against epitopes of interest can be screened for various properties; i.e., for isotype and epitope affinity.

Antibodies, both monoclonal and polyclonal, which are directed against epitopes are particularly useful in diagnosis, and those which are neutralizing are useful in passive immunotherapy. Monoclonal antibodies, in particular, may be used to raise anti-idiotype antibodies. Anti-idiotype antibodies are immunoglobulins which carry an "internal image" of the antigen of the infectious agent against which protection is desired.

Techniques for raising anti-idiotype antibodies are known in the art. These anti-idiotype antibodies may also be useful for treatment of viral and/or bacterial diseases, as well as for an elucidation of the immunogenic regions of viral and/or bacterial antigens.

It is also possible to use fragments of the antibodies described above, for example, Fab fragments.

The invention will be described with reference to the following Examples which are intended to be illustrative only and not limiting. The Examples refer to the following Figures.

BRIEF DESCRIPTION OF THE FIGURES

FIG. 6 shows the amino acid sequence comparison between the predicted core proteins of HCV and GBV-B.

DETAILED DESCRIPTION OF THE FIGURES

FIG. 1

Figure 1A:
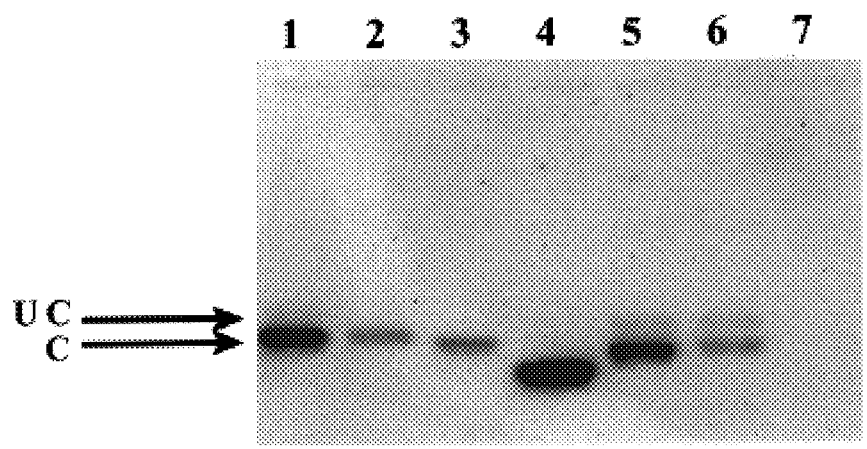
FIG. 1 shows Western blots probed with antibodies to HCV core protein

Analysis of the core proteins made by the pSFV and pgHCV constructs.

A. Western blot analysis of extracts prepared from cells which were harvested 20 hours after electroporation. Aliquots of extracts containing the same number of cell equivalents were analyzed with antibody JM122. The samples were from cells electroporated with RNA from the following constructs: lane 1, pSFV.1-195; lane 2, pSFV.1-173; lane 3, pSFV.1-169; lane 4, pSFV.1-153; lane 5, pSFV.Δ155-161; lane 6, pSFV. Δ161-166; lane 7, no RNA.

Arrows denote the forms of core which have (labeled C) and have not (labeled UC) been cleaved at the internal processing site.

B. In vitro translation of core proteins. Products of reactions were electrophoresed on a 10% polyacrylamide gel and detected by autoradiography. The samples were from reactions containing the following constructs: lane 1, pgHCV.1-195; lane 2, pgHCV.1-173; lane 3, pgHCV.1-153.

FIG. 2

Confocal images of the intracellular localization of core proteins and lipid droplets. BHK C13 cells were harvested 20 hours after electroporation and fixed with 4% paraformaldehyde, 0.1% Triton X-100. Indirect immunofluorescence was performed with antibody JM122 and an anti-mouse secondary antibody conjugated with FITC. Lipid droplets were stained with oil red O. Panels A, D, G, J, M, P, S and V show the distributions of core protein. Panels B, E, H, K, N, Q, T and W show the locations of lipid droplets. Panels C, F, I, L, O, R, U and X are merged images of core protein and lipid droplets. Cells were electroporated with RNA from the following constructs: panels A, B and C, pSFV.1-195; panels D, E and F, pSFV.1-173; panels G, H and I, pSFV.1-169; panels J, K and L, pSFV.1-153; panels M, N and O, pSFV.Δ155-161; panels P, Q and R, pSFV.Δ161-166; panels S, T and U, pSFVΔ125-144; panels V, W and X, pSFV.1-124, 145-152.

FIG. 3

Effect of expression of core proteins on the ability to detect ADRP in BHKC13 cells by confocal microscopy. Cells were harvested 20 hours after electroporation and fixed with methanol. ADRP was detected with anti-adipophilin antibody and core protein with 308 antisera. Secondary antibodies were an anti-mouse IgG conjugated with FITC (for anti-adipophilin) and anti-rabbit IgG conjugated with Cy5 (for 308 antisera). Panels A, D, G, J, M and P are images of ADRP localization. Panels B, E, H, K, N, and Q are images of core distribution. Panels C, F, I, L, O and R show the merged images of core and ADRP distributions. Cells were electroporated with RNA from the following constructs: panels A, B and C, pSFV.1-195; panels D, E and F, pSFV.1-173; panels G, H and I, pSFV.1-169; panels J, K and L, pSFV.1-153; panels M, N and 0, pSFV.Δ155-161; panels P, Q and R, pSFV.Δ161-166.

FIG. 4

Effect of expression of core proteins on the ability to detect ADRP in MCA RH7777 cells by confocal microscopy. Cells were examined as described in the legend for FIG. 3.

FIG. 5

Effect of expression of core protein on the abundance of ADRP. BHK C13 cells were electroporated with RNA from pSFV.1-195 and pSFV.1-153 and extracts were prepared at the times indicated following electroporation. Aliquots of cell extracts were electrophoresed on 10% polyacrylamide gels and then the proteins were transferred to nitrocellulose membrane for Western blot analysis. The upper panels show membranes probed with JM122 antibody while, in the lower panels, membranes were probed with anti-adipophilin antibody. Bands corresponding to core proteins, expressed from pSFV.1-195 and pSFV.1-153, and ADRP are arrowed.

EXAMPLES

Materials and Methods

Cell Lines

Baby hamster kidney (BHK) C13 cells were maintained in Glasgow modified Eagle's medium supplemented with 10% newborn calf serum, 100 IU/ml penicillin/streptomycin and 5% tryptose phosphate broth. The rat hepatoma cell line, MCA RH7777, was maintained in minimal essential Eagle's medium supplemented with 20% foetal bovine serum, 100 IU/ml penicillin/streptomycin, 1×non-essential amino acids and 2 mM L-glutamine.

Immunological Reagents

Antibody JM122 was a mouse monoclonal antibody raised against a purified fusion protein, expressed in bacteria, which was composed of the N-terminal 118 amino acid residues of core protein encoded by HCV strain Glasgow linked to a histidine tag. Antisera 308 was raised in rabbits against a branched peptide ([A/P]KPQRKTKRNT[I/N]RRPQDVKFPGG)$_8$K$_7$A. The peptide consists of residues 5–27 of core protein encoded by HCV strain Glasgow (SEQ ID. No. 1). The two degenerate sites at positions 1 and 12 were introduced to obtain antisera which would be reactive against core proteins from other isolates. The adipophilin antibody was obtained from Cymbus Biotechnology Ltd.

Secondary antibodies were obtained from Sigma with the exception of Cy5 conjugated goat anti-rabbit IgG which was obtained from Amersham.

Construction of Plasmids

Plasmids containing the coding region for the core protein of HCV strain Glasgow were obtained by combining fragments from two constructs called core.pTZ18 and 5'-ΔNS2 (provided by M. McElwee and R. Elliott). Core.pTZ18 possesses nucleotide residues 337–915 of the HCV strain Glasgow genome and 5'-ΔNS2 contains residues 1–2895. DNA fragments from these plasmids were combined in a vector called pGEM1 to give a construct termed pgHCV.CE1E2. This plasmid contains nucleotide residues 337–2895 of the HCV strain Glasgow genome and therefore encodes the core, E1 and E2 proteins of this isolate.

For cloning purposes, the sequences immediately upstream of residue 337 were modified to contain the recognition sequences for Bgl II and Kpn I restriction enzyme sites and immediately downstream of residue 2895, an oligonucleotide was inserted which encodes a translational stop codon followed by the sequences for a Bgl II restriction enzyme site. To create pgHCV.CE1E2, a Bgl II DNA fragment containing the core, E1 and E2 sequences was inserted into the Bam HI site of pGEM1; this plasmid was further modified by introducing a Bgl II enzyme site at the Eco RI site in the pGEM backbone. Construction of a derivative plasmid, pgHCV.1-195 was achieved by inserting an oligonucleotide (GCTGAGATCTA) that had both a translational stop codon and the sequences for a Bgl II enzyme site between a Fsp I enzyme site at residue 925 in the HCV genome and a Hind III enzyme in the pGEM backbone. Thus, pgHCV.1-195 encodes the N-terminal 195 amino acids of HCV strain Glasgow. The nucleotide and predicted amino acid sequence of this region of HCV strain Glasgow is shown in SEQ ID. No. 1. From pgHCV.1-195, the following series of constructs were made which had various regions of the HCV coding region removed (in 1 to 3 and 6, the numbers following pgHCV represent the amino acid residues of HCV strain Glasgow encoded by each construct):

1. pgHCV.1-173 was constructed by inserting an oligonucleotide GTAACCTTCCTG GTTGCTCTTGAGATCTA between the Bst EII (at nucleotide residue 841 in the HCV strain Glasgow genome) and Hind III enzyme sites (located in the pGEM backbone) in pgHCV.1-195.

2. pgHCV.1-169 was constructed by inserting an oligonucleotide GTAACCTTTGAG ATCTA between the Bst EII (at nucleotide residue 841 in the HCV strain Glasgow genome) and Hind III enzyme sites (located in the pGEM backbone) in pgHCV.1-195.

3. pgHCV.1-153 was constructed by inserting an oligonucleotide CTGGCGCATTGA GATCTA between the Bst XI (at nucleotide residue 792 in the HCV strain Glasgow genome) and Hind III enzyme sites (located in the pGEM backbone) in pgHCV.1-195.

4. pgHCV.Δ155-161 was constructed by inserting an oligonucleotide CTGGCCCATG GTGTTAACTATGCAACAG between the Bst XI and Bst EII enzyme sites (at nucleotide residues 792 and 841 respectively in the HCV strain Glasgow genome) in pgHCV.1-195. This construct lacks the nucleotide sequences encoding residues 155 to 161 of the core protein of HCV strain Glasgow.

5. pgHCV.Δ161-166 was constructed by inserting another oligonucleotide CTGGCCCATGGCGTCCGGGTTCTGGAAGACG between the Bst XI and Bst EII sites in pgHCV.1-195. This construct lacks the nucleotide sequences encoding residues 161 to 166 of the core protein of HCV strain Glasgow.

6. pgHCV.1-124, 145-152 was constructed by inserting an oligonucleotide CGATA GAGGCGCTGCCAGGGCCCTGGCGTGAGATCTA between the Cla I (at nucleotide residue 710 in the HCV strain Glasgow genome) and Hind III enzyme sites (located in the pGEM backbone) in pgHCV.1-195.

7. pgHCV.Δ125-144 was constructed by inserting a 400 bp Kpn I/Bst XI DNA fragment from pgHCV.1-124, 145-152 (which contains residues 1–124 and 145–152) into a 2970 bp Kpn I/Bst XI DNA fragment from pgHCV.1-195 (which contains residues 153–195).

For expression in tissue culture cells, Bgl II DNA fragments carrying the relevant HCV sequences were prepared from the pgHCV plasmid series and inserted into the Bam HI site of a Semliki Forest virus vector pSFV1. The resultant plasmids were termed the pSFV. series (e.g. pSFV.1-195).

In Vitro Translation

Proteins were translated in vitro using a coupled transcription/translation kit supplied by Promega. Reactions used 1 μg of DNA as template and were carried out according to manufacturer's instructions.

In Vitro Transcription

Prior to electroporation, RNA was transcribed in vitro from the appropriate pSFV plasmid which had been linearised at a Spe I enzyme site. Typical reactions were carried out in a volume of 20 □1 and contained 40 mM Tris (pH 7.5), 6 mM $MgCl_2$, 2 mM spermidine, 10 mM NaCl, 1 mM DTT, 1 mM ATP, 1 mM CTP, 1 mM UTP, 0.5 mM GTP, 1 mM $m^7G(5')ppp(5')G$ cap analogue, 50 units Rnasin, 50 units SP6 RNA polymerase and 2 μg linearised DNA. Reactions were performed at 37° C. for 2 hours. Products of the reaction were analyzed by agarose gel electrophoresis to examine the quality and quantity of RNA synthesized prior to use in electroporations.

Preparation of Cells Competent for Electroporation

Cells were washed and treated with trypsin for detachment from tissue culture containers. Detached cells were suspended in 20 ml of growth medium and centrifuged at 100 g for 5 min at room temperature. Cell pellets were suspended in 50 ml of PBSA and centrifuged as previously. Pellets were suspended in PBSA at a final concentration of about $2 \times 10^7$ cells/ml.

Electroporation of Cells and Preparation of Cell Extracts 0.8 ml of competent cells were mixed with in vitro transcribed RNA in an electroporation cuvette (0.4 cm gap) and pulsed twice at either 1.2 kV, 25 μF (for BHK C13 cells) or 0.36 kV, 960 μF (for MCA RH7777 cells). Between pulses, the cell/RNA suspension was gently mixed. Following electroporation, cells were diluted in growth medium and seeded onto either tissue culture dishes or coverslips in 24-well tissue culture plates and then incubated at 37° C.

To prepare extracts, electroporated cells were harvested by removing the growth medium and washing the cell monolayers with PBS. Cells were scraped into PBS and pelleted by centrifugation at 100 g for 5 mins at 4° C. The cell pellet was solubilised in sample buffer consisting of 160 mM Tris (pH 6.7), 2% SDS, 700 mM β-mercaptoethanol, 10% glycerol, 0.004% bromophenol blue.

Alternatively, sample buffer was added directly to cells which had been washed with PBS. Cells were solubilised at a concentration of approximately $4 \times 10^6$ cell equivalents per ml sample buffer. Samples were heated to 100° C. for 5 mins to fully denature proteins and nucleic acids.

SDS-PAGE and Western Blot Analysis

Samples were prepared for electrophoresis and proteins were separated on polyacrylamide gels cross-linked with 2.5% (wt/wt) N,N'-methylene bisacrylamide using standard techniques. Polypeptides were detected either by autoradiography or by staining using Coomassie brilliant blue.

For Western blot analysis, proteins were separated on polyacrylamide gels and transferred to nitrocellulose membrane using standard techniques. The nitrocellulose membrane was blocked in 3% gelatin, 20 mM Tris (pH 7.5), 500 mM NaCl for at least 6 hours at 37° C. prior to incubation with the primary antibody. Incubations with the primary antibody (diluted to 1/500 for adipophilin antibody and 1/1000 for JM122) were performed in 1% gelatin, 20 mM Tris (pH 7.5), 500 mM NaCl, 0.05% Tween 20 at either room temperature or 37° C. for approximately 3–4 hours. Following extensive washing with 20 mM Tris (pH 7.5), 500 mM NaCl, 0.05% Tween 20, the membrane was incubated for 2 hours at room temperature with anti-mouse IgG conjugated with horse radish peroxidase in the same solution as for the primary antibody and at a dilution of 1/1000. Bound antibody was detected by enhanced chemiluminescence.

Indirect Immunofluorescence and Staining of Lipids

Cells on 13 mm coverslips were fixed in either methanol at −20° C. or 4% paraformaldehyde, 0.1% Triton X-100 (prepared in PBS) at 4° C. for 30 mins. Following washing with PBS and blocking with PBS/CS (PBS containing 1% newborn calf serum), cells were incubated with primary antibody (diluted in PBS/CS at 1/200 for JM122 antibody, 1/1000 for 308 antisera and 1/100 for adipophilin antibody) for 2 hours at room temperature. Cells were washed extensively with PBS/CS and then incubated with conjugated secondary antibody (either anti-mouse or anti-rabbit IgG raised in goat) for 2 hours at room temperature. Cells were washed extensively in solutions of PBS/CS followed by PBS and finally $H_2O$ before mounting on slides using Citifluor. Samples were analyzed using a Leiss LSM confocal microscope.

Following incubation with both antibodies and washing, lipid droplets were stained in paraformaldehyde-fixed cells by briefly rinsing coverslips in 60% propan-2-ol followed by incubation with 0.5 ml 60% propan-2-ol containing oil red O for 1.5–2 mins at room temperature. Coverslips were briefly rinsed with 60% propan-2-ol, washed with PBS and $H_2O$ and mounted as described above. The oil red O staining solution was prepared from a saturated stock of approximately 1% oil red O dissolved in propan-2-ol. Before staining, the stock was diluted with $H_2O$ and then filtered.

Results

Example 1

Expression of HCV Core Protein and Variants in Tissue Culture Cells

Presently, there is no system available for propagating HCV in tissue culture cells. Therefore, expression of HCV gene products necessitates the use of heterologous expression systems. For short-term expression in mammalian cells, a variety of viral vectors have been utilized including vaccinia virus, Sendai virus and adenovirus. A further alternative is the Semliki Forest virus (SFV) system in which in vitro transcribed RNA, that encodes the SFV replication proteins as well as a heterologous protein but not the SFV structural proteins, is introduced into tissue culture cells. Introduction of nucleic acid into cells may be achieved by several routes but, in the examples given, the method of choice is electroporation.

BHK cells were electroporated with RNA from the series of pSFV constructs. 20 hours following electroporation, cells were harvested and extracts prepared. Samples were electrophoresed on a 10% polyacrylamide gel and, following electrophoresis, the proteins were transferred to nitrocellulose membrane for Western blot analysis.

Probing the membrane with the core-specific monoclonal antibody JM122 revealed a major single species in each sample which corresponds to core protein. The apparent molecular weights of the proteins made by pSFV.1-195 and two truncated variants, pSFV.1-173 and pSFV.1-169, are approximately 21 kDa and are almost identical (FIG. 1A, lanes 1–3). Cleavage between the core and E1 coding regions occurs between residues 191 and 192. However, there is additional data which reveals that the core protein is further processed by cleavage around residue 174 (Moradpour et al., 1996) this cleavage site will be referred to as the internal processing site. The precise residue at which this second cleavage event occurs is not known. Hence, in agreement with FIG. 1A, lanes 1–3, it would be predicted that the three constructs named above would generate products of similar molecular weights.

Figure 1B:
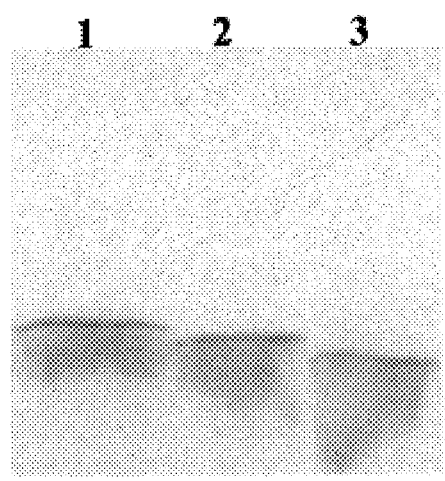
Figures 2A, 2B, 2C:
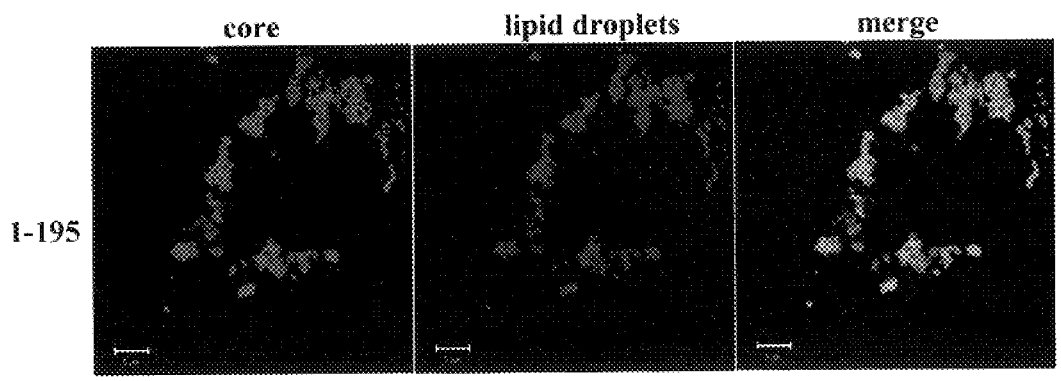
FIG. 2 shows confocal microscopy images of the intracellular localization of core proteins and lipid droplets.
Figures 2D, 2E, 2F:
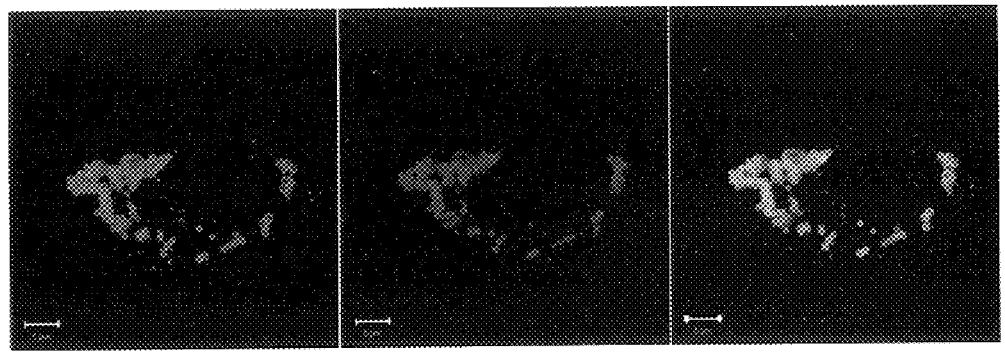
Figures 2G, 2H, 2I:
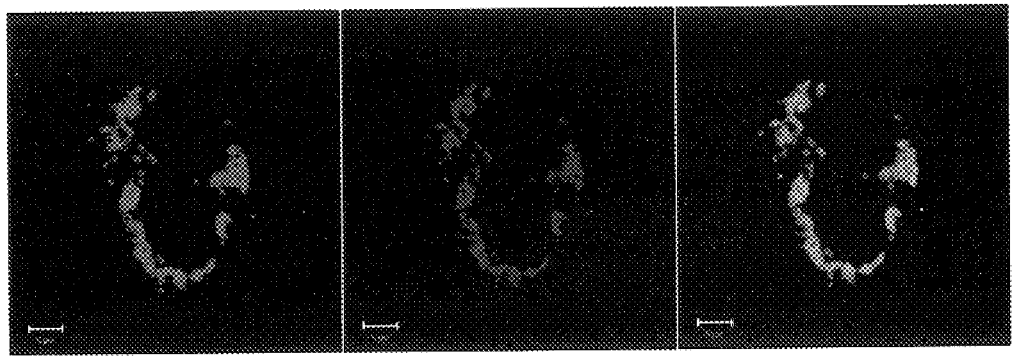
Figures 2J, 2K, 2L:
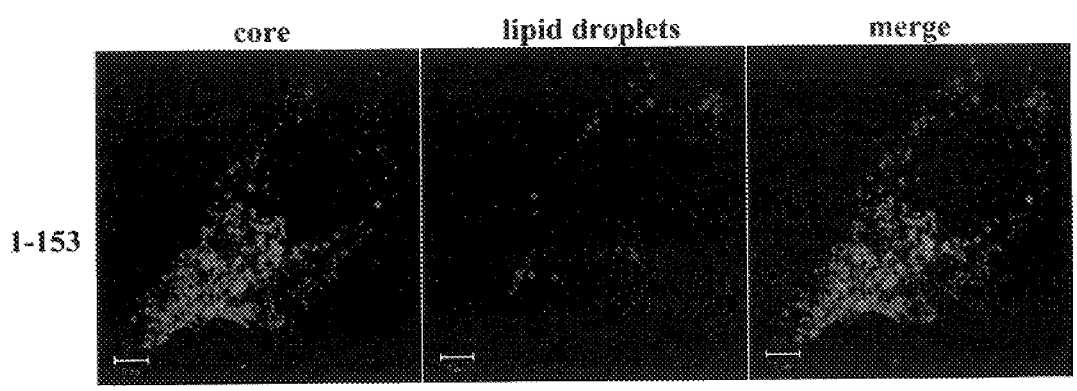
Figures 2M, 2N, 2O:
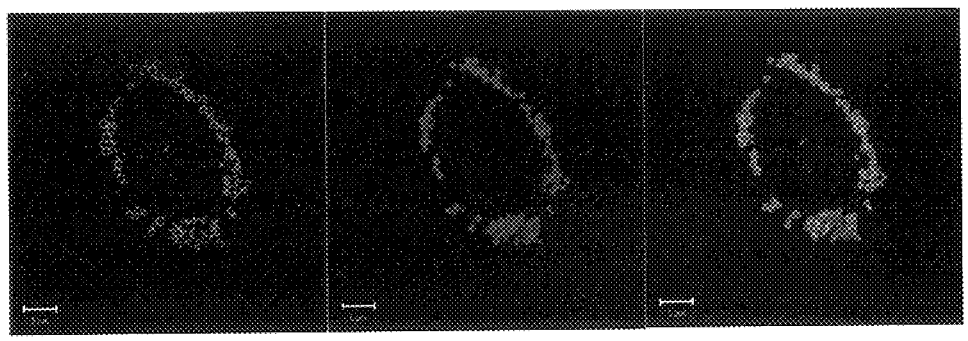
Figures 2P, 2Q, 2R:
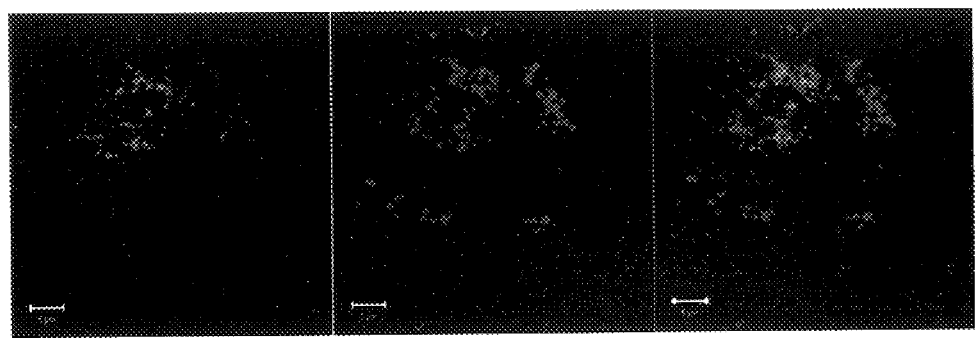
Figures 2S, 2T, 2U:
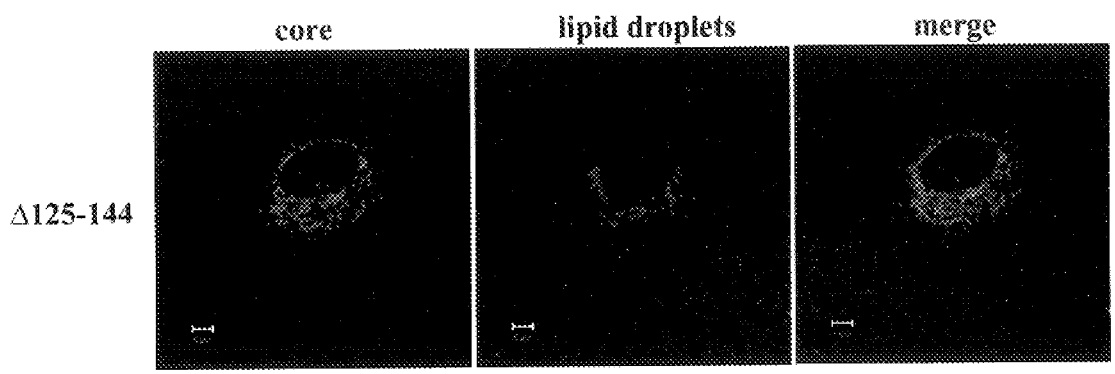
Figures 2V, 2W, 2X:
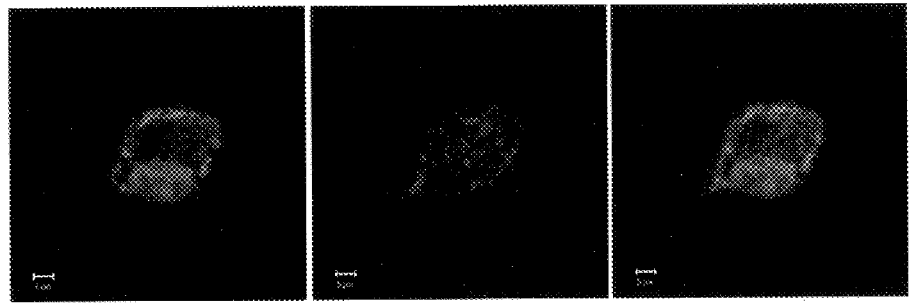
Figures 3A, 3B, 3C:
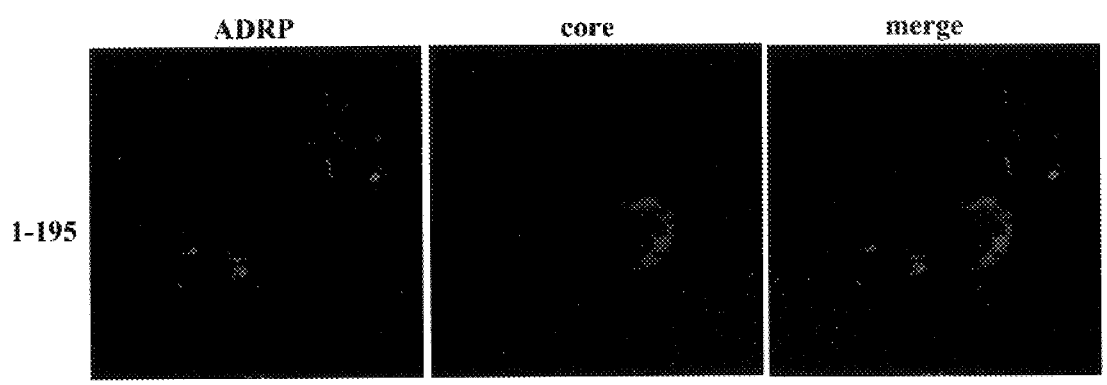
FIG. 3 shows confocal microscopy images of cells illustrating the effect of expression of HCV core proteins on the ability to detect ADRP in BHKC13 cells.
Figures 3D, 3E, 3F:
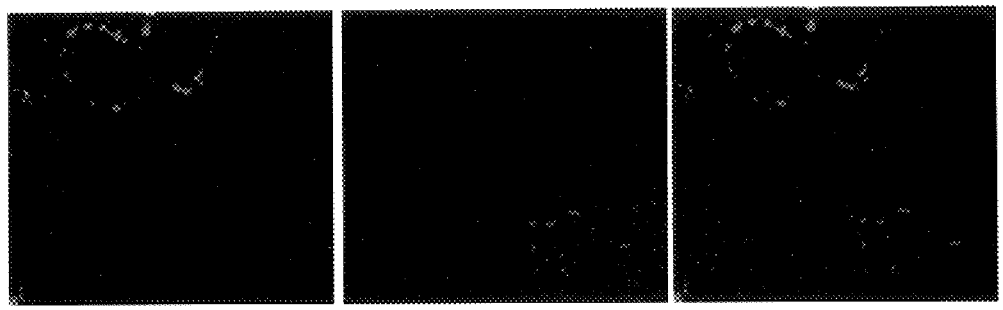
Figures 3G, 3H, 3I:
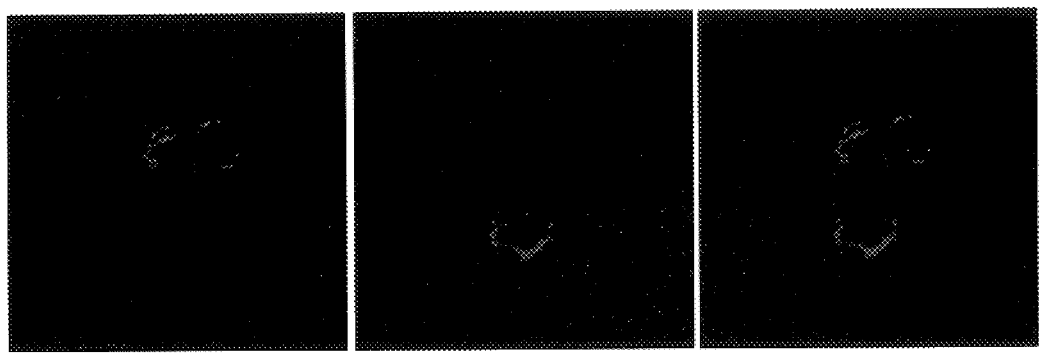
Figures 3J, 3K, 3L:
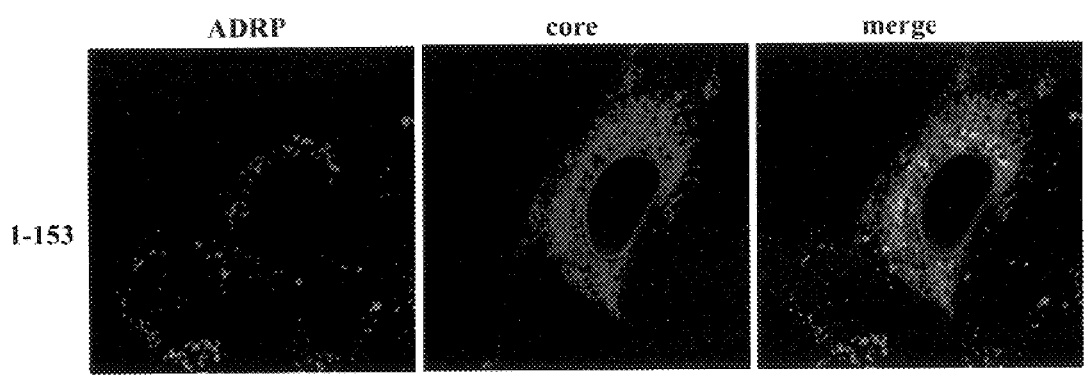
Figures 3M, 3N, 3O:
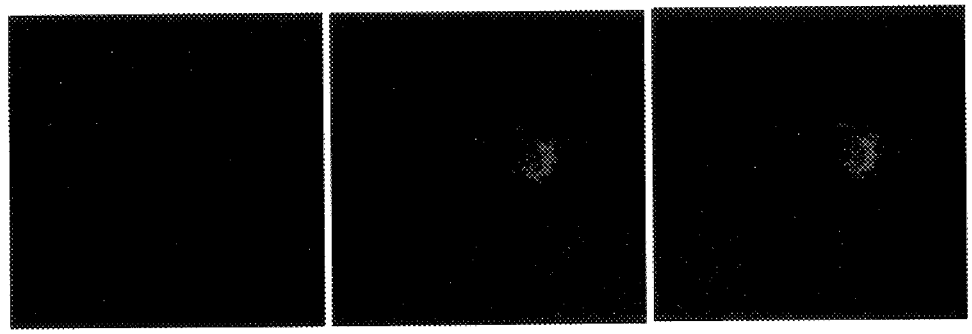
Figures 3P, 3Q, 3R:
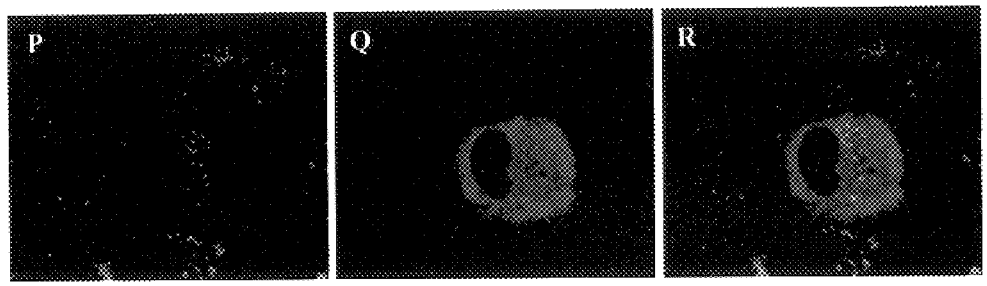
Figures 4A, 4B, 4C:
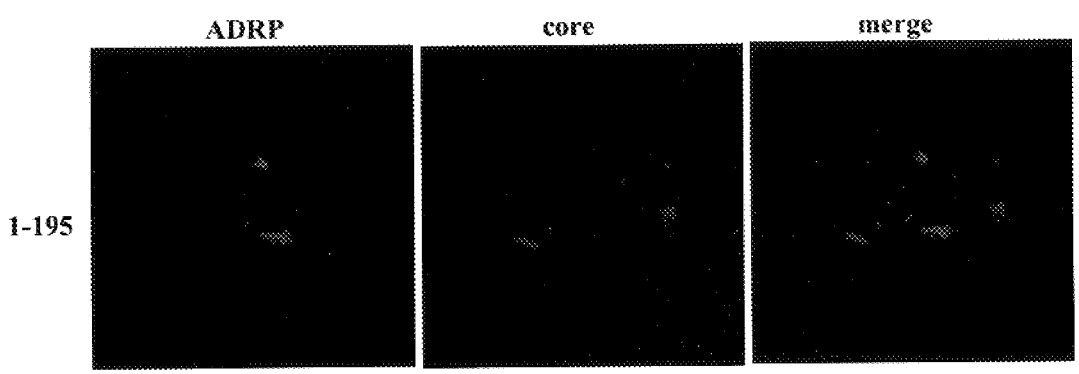
FIG. 4 shows confocal microscopy images of cells illustrating the effect of expression of HCV core protein on the abundance of ADRP.
Figures 4G, 4H, 4I:
Figures 4J, 4K, 4L:
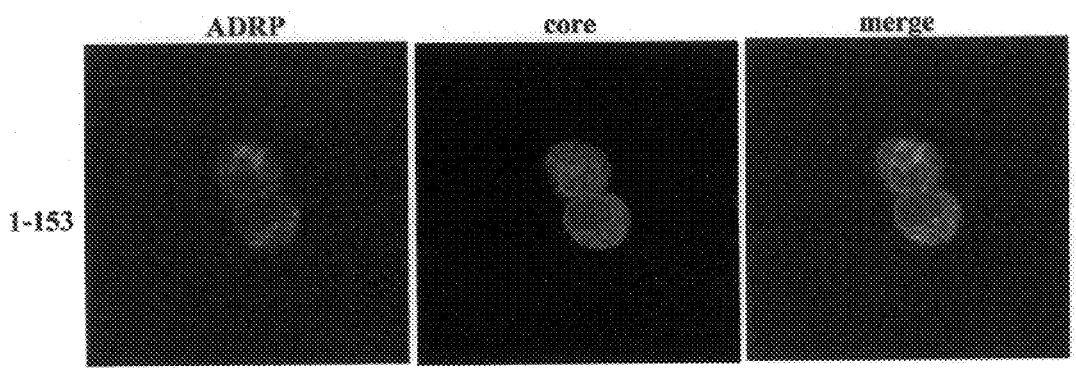
Figures 4M, 4N, 4O:
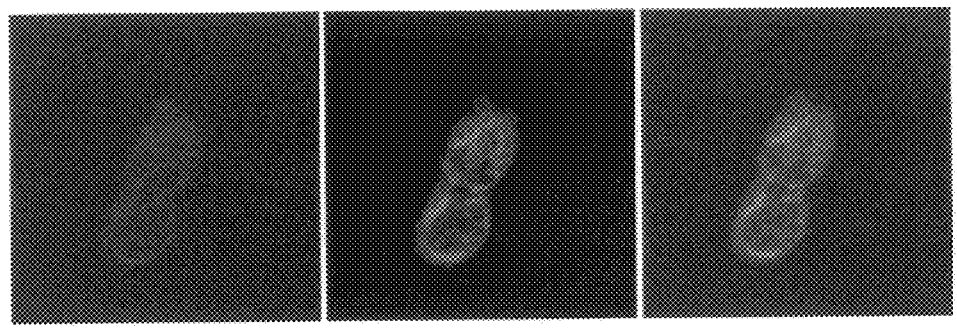

Additional evidence for a cleavage event close to residues 169–173 occurring within tissue culture cells is shown in FIG. 1B. Here, polypeptides translated in vitro from the pGEM versions of 3 core variants reveal that the unprocessed species made from pgHCV.1-195 is larger than that from pgHCV.1-173 (compare lanes 1 and 2). As would be predicted from the coding sequences for the third truncated form of core, the major species synthesized from pSFV.1-153 has a lower apparent molecular weight than that from pSFV.1-195 (FIG. 1A, compare lanes 1 and 4). The major species made by the internal deletion mutants pSFV.Δ155-161 and pSFV.Δ161-166 are intermediate in size between those produced by pSFV.1-195 and pSFV.1-153 (FIG. 1A, lanes 5 and 6). Again, this agrees well with predictions based on the number of amino acids removed in these variants (7 in pSFV.Δ155-161 and 6 in pSFV.Δ161-166). It is also evident that there is a significant amount of material produced by the two internal deletion variants which has a higher molecular weight than the fully processed form of core. This presumably represents reduced cleavage at the internal processing site which may result from the removal of certain residues in these mutants which are necessary for filly efficient processing. To conclude, the core proteins and its variants produced by the SFV constructs can be detected by a core-specific antibody and their apparent molecular weights are in agreement with predictions from the nucleotide sequences and previously published data.

Example 2

Intracellular Distribution of HCV Core Protein

Previous studies have revealed that the HCV core protein can associate with lipid droplets within the cytoplasm of cells (Barba, G. et al., 1997; Moradpour, D. et al., 1996. This conclusion was arrived at by combining the techniques of immune electron microscopy with the ability to stain lipid with osmium tetroxide. However, this method suffers from the disadvantages that it is time-consuming and osmium tetroxide can stain other biological molecules (e.g proteins) in addition to lipid. Therefore, we developed a method for detecting proteins firstly by indirect immunofluorescence followed by staining of lipid droplets with the oil-soluble colourant oil red O. Combined with the method of confocal microscopy, it is possible to visualize the intracellular localisations of core protein and lipid droplets separately and together. A typical example is shown in FIG. 2, panels A–C. Here, BHK C13 cells have been electroporated with pSFV.1-195 RNA and, following incubation at 37° C. for 20 hours, the cells have been examined by both indirect immunofluorescence and staining with oil red O. In panel A, the core protein produced by pSFV.1-195 is seen to locate to vesicular structures in the cytoplasm. Panel B reveals the distribution of lipid droplets in the same cell. By merging these data (panel C), it is evident that core protein is sited around the lipid droplets. These data therefore agree with previously published results for constructs expressing the full-length coding region of core.

Example 3

Association of HCV Core Protein with Intracellular Lipid Droplets Requires Amino Acids 161 to 166 and 125 to 144

Results with the constructs which produce truncated forms of core protein indicate that proteins consisting of 173 and 169 amino acids of the core coding region also locate to droplets (FIG. 2, panels D–I). By contrast, expressing only the N-terminal 153 residues results in loss of localisation to droplets and a diffuse cytoplasmic distribution is observed (FIG. 2, panels J–L). Thus, residues of core protein between amino acids 154 and 169 are required for localisation to droplets. Studies with the internal deletion mutants pSFV.Δ155-161 and pSFV.Δ161-166 further examined segments within this 16 amino acid region which may be important for core protein localisation. From the resultant data, removal of residues between 155 and 161 did not affect lipid droplet association whereas removal of residues between 161 and 166 gave a diffuse cytoplasmic pattern (FIG. 2, compare panels M–O with P–R). Hence, between residues 154 and 169, amino acids from 161 to 166 play an essential role in the ability of core protein to locate to lipid droplets.

Further analysis of other internal deletion mutants (which removed residues 9–43, 4–75 and 80–118) showed that the core proteins made by these constructs continued to associate with lipid droplets (data not shown). Hence, these regions are dispensable for binding to droplets. However, a construct expressing a core variant in which residues 125 to 144 had been deleted failed to distribute to droplets and gave a diffuse cytoplasmic fluorescence (FIG. 2, panels S, T and U). This mutant therefore identifies a second region in addition to the segment between 161 and 166 which is necessary for association with droplets. The data suggest that both sets of sequences are required for targeting to lipid droplets. In agreement with these data, a core variant which is truncated at residue 152 and lacks amino acids 125 to 144 also fails to bind to droplets (FIG. 2, panels V, W and X). Additionally, this protein, in which both sets of targeting sequences are deleted, is present in low amounts in electroporated cells as a consequence of degradation.

Example 4

Effect of Localisation of Core Protein on the Lipid Droplet Associated Protein ADRP At present, there are few proteins identified in mammalian cells which are known to associate with lipid droplets. One protein which has been recently identified is ADRP which is ubiquitously expressed in a number of tissue culture cell lines; ADRP mRNA has also been detected in a range of tissue types in mice. To examine whether the localisation of core to lipid droplets had any affect on ADRP, BHK C13 cells were electroporated with the series of pSFV constructs expressing core protein and its variants. An example of the data is shown in FIG. 3. Panels A to C show images of three cells following electroporation with pSFV.1-195, only one of which contains core protein (Panel B). Immunofluorescent results with the adipophilin antibody (panel A) reveal that ADRP is located on vesicular structures, consistent with its previously assigned association with lipid droplets. The protein is readily detected in the cells which do not express core protein, however, it is considerably reduced in abundance in the core-expressing cell. Observations from this and a series of other experiments consistently revealed that cells expressing core protein from pSFV.1-195 either lacked or contained barely detectable amounts of ADRP.

Nonetheless, some cells were also found in which both core protein and ADRP were present; in general, such cells gave reduced fluorescence for the core protein. Hence, it was concluded that the loss of ADRP was related to the levels of expression of core in individual cells. Results with the variants of core which continue to locate to lipid droplets gave identical data (see panels D–I and M–O). Thus, the majority of cells expressing core protein from constructs pSFV.1-173, pSFV.1-169 and pSFV.Δ155-161 contained quantities of ADRP which were barely detectable. By contrast, ADRP continued to be readily found in cells producing core proteins from pSFV.1-153 and pSFV.Δ161-166, the variants which do not associate with lipid droplets (see panels J–L and P–R). Thus, association of core protein with lipid droplets correlates with a loss of ability to detect ADRP by immunofluorescence. Any cell type specificity for this affect was tested by performing identical experiments in the rat hepatoma cell line, MCA RH7777. In these cells, core protein and its variants gave identical results for their ability to associate with lipid droplets and this again correlated with the levels of ADRP detected in core-expressing cells (FIG. 4). Thus the effect of core protein on ADRP is not cell-type specific.

Example 5

The Ability of Core Protein to Associate with Lipid Droplets Induces a Loss of ADRP The immunofluorescence data revealed that the association of core protein and its variants with lipid droplets led to an inability to detect ADRP. It was possible that this was due to masking of ADRP by core. To examine directly the effect of core protein on the levels of ADRP, Western blot analysis was performed on cell extracts prepared at various times following electroporation with either pSFV.1-195 or pSFV.1-153 RNA. In parallel, immunofluorescence analysis was also performed on these cells and this revealed that expression of the core protein produced by the two RNAs was apparent in greater than 90% of cells.

Figure 5:
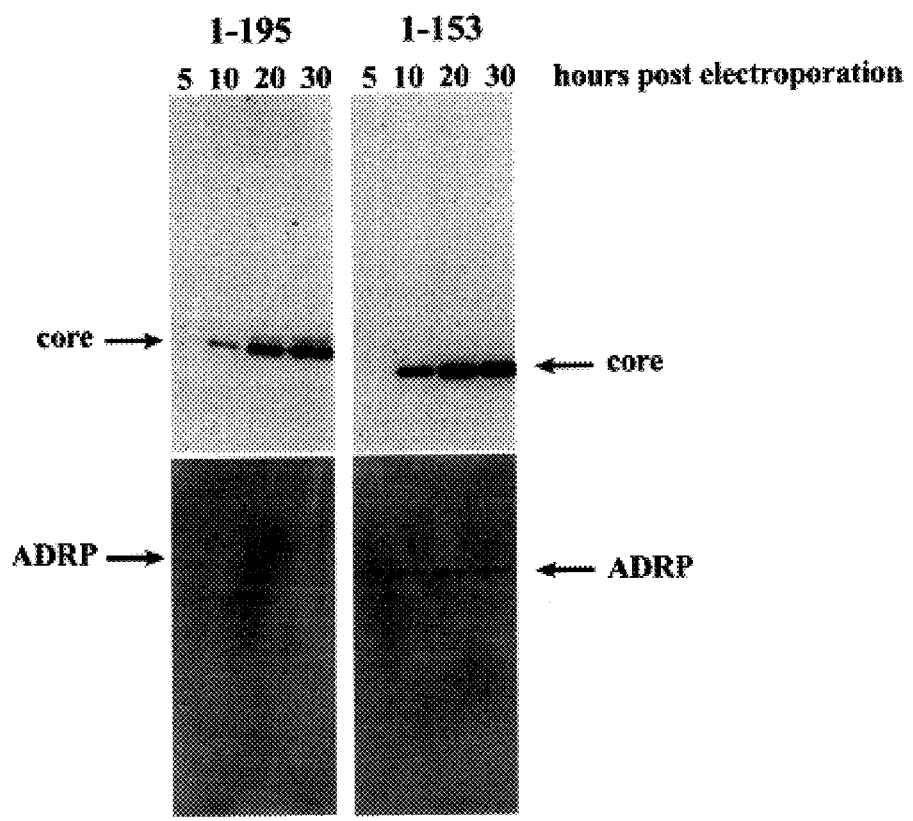
FIG. 5 shows Western blots probed with antibodies to HCV core protein and adipophilin.

Analysis with antibody JM122 indicated that core protein could be detected from both constructs at 10 hours following electroporation and peaked by about 20 hours (FIG. 5). The abundance of core protein produced by the two constructs was very similar by this time-point. From analysis of these samples with the ADRP-specific antibody, it is apparent that there is no change in the abundance of ADRP following electroporation with the pSFV.1-153 RNA. A third set of cells in this experiment which was electroporated with SFV RNA which expresses the HCV E1 and E2 proteins also showed no reduction in ADRP levels with time. By contrast, there is a rapid reduction in ADRP levels to barely detectable quantities which mirrors the rise in core protein made from pSFV.1-195.

From staining of polyacrylamide gels with Coomassie brilliant blue, there were approximately equivalent amounts of protein in all samples. In addition, probing the membranes with another antibody for a endoplasmic reticulum-specific protein, calnexin, indicated that both pSFV.1-195 and pSFV.1-153 samples had similar quantities of this protein at the various times following electroporation. This affect of core expression on ADRP was consistently found in other experiments. Thus, the association of core protein with lipid droplets directly correlates with a specific reduction in the abundance of this protein in cells.

Example 6

Targeting of a Protein of Interest Fused to an HCV Targeting Sequence

To determine whether HCV core is capable of targeting a linked protein of interest to intracellular lipid globules, a fusion construct composed of HCV core protein sequences linked to herpes simplex virus type 1 (HSV-1) VP22 protein (encoded by gene UL49) is made.

The fusion construct comprises (from the N-terminus to the C-terminus)
1) The N-terminal 8 residues or the N-terminal 43 residues of HCV core.
2) Segments of the HSV-1 UL49 gene encoding residues 6–275 and 173–275.
3) An epitope tag consisting of residues ERKTPRVTGG. (McLauchlan, J. et al., 1994).
4) C-terminal residues of HCV core from 120–195 and 120–169.

It is also possible to use constructs wherein the N-terminal residues of HCV and the C-terminal residues of HCV are contiguous and at the C-terminal or N-terminal end of the UL49 coding sequence (i.e. 2, 3, 1, 4 or 1, 4, 2, 3 as denoted above).

These constructs will be expressed using the SFV vector system and their ability to associate with lipid droplets will be assessed by immunofluorescence and oil red O-staining as described above. The antibody used to detect the epitope tag is the anti-HCMV nuclear antigen antibody (MAb 9220) supplied by Capricorn Products. This antibody is also used to verify by Western blot analysis that the fusion protein is of the predicted size and its abundance in comparison with core constructs.

Example 7

Identification of a Domain Required to Direct Core Protein of HCV and GB Virus B to Lipid Droplets In this example we have identified a conserved domain that is present in equivalent structural proteins encoded by HCV and GBV-B and directs these proteins to lipid storage compartments.

GBV-B is a virus called GB virus-B. Information on GB virus-B has been presented by Beames et al (2000, Journal of Virology vol 74 No. 24, pp 11764–11772) and Lanford et al (2001, Journal of Virology vol 75 No. 17, pp 8074–8081).

GBV-B was isolated from tamarins but the natural host of the virus is not known. The GBV-B core protein is described in the example below. The nucleic acid sequence of GBV-B is shown in Genbank Accession No. NC001655. GBV-B is the closest known related virus to HCV in terms of sequence identity (29). GBV-B core protein is an example of a homologue of HCV core protein. An alignment of HCV and GVB-B amino acid sequence is shown in FIG. 6. Furthermore, GVB-B is an example of a lipid globule targeting sequence.

Lipid droplets are intracellular storage organelles that are found in all eukaryotic organisms and some prokaryotes (reviewed in 1–3). They consist of a core of neutral lipid, comprising mainly triacylglycerols and/or cholesterol esters, surrounded by a monolayer of phospholipids. Bounding the phospholipid layer is a proteinaceous coat. In mammalian cells, the principal lipid droplet binding proteins that have been identified are adipophilin (also called adipocyte differentiation-related protein, ADRP; 7, 8) and a related family of proteins termed the perilipins (9–11). Adipophilin is present in a wide range of cell types and in increased quantities in certain diseases where intracellular lipid accumulation is evident (12–14). By contrast, expression of the perilipins is restricted to adipocytes and steroidogenic cells (15, 16).

In addition to adipophilin and the perilipins, the core protein encoded by hepatitis C virus (HCV) also associates with lipid droplets in mammalian cells (17–19). HCV is the sole member of the hepacivirus genus that is incorporated into the Flaviviridae family along with two other genera, the flavi- and pestiviruses. All of the Flaviviridae are positive-sense, single stranded RNA viruses that have similar genome arrangements and share sequence similarities. HCV core is a structural component of the virus particle and, by analogy with flavi- and pestiviruses, it is likely to be the sole component of the capsid (20, 21). The protein is generated from a polyprotein encoded by the viral genome by cleavage at the endoplasmic reticulum (ER; 22–26). Expression of core can lead to the genesis of lipid droplets in tissue culture cells (18) and the development of steatosis in transgenic mice (27). Moreover, interaction between core and apolipoprotein AII, a component of lipid droplets, has been demonstrated (28). These data indicate that, not only does core associate with lipid droplets, but it also may have the capacity to influence metabolic events within the cell involving the storage of lipid.

To understand the significance of the interaction between HCV core and lipid droplets, a region within the viral protein that is essential for its association with these storage organelles had been identified (19). In this example, studies have been carried out to determine whether there is any similarity between the sequences within this region and those of GBV-B, which has significant sequence identity to HCV although, as yet, it remains unclassified among the genera of the Flaviviridae (29). GBV-B shares a tropism for liver hepatocytes with HCV and is infectious in tamarins (30, 31). Thus, it has been suggested that GBV-B infection of tamarins may be a surrogate model system for HCV infection of humans (31). However, few comparative studies between equivalent proteins encoded by the two viruses have been conducted.

TABLE 1

Oligonucleotides used to generate constructs.

| Name | Oligonucleotide Sequence | Nucleotide Position[a] |
|---|---|---|
| HCV 1 | CAT GGG GTA CAT AGC GCT CGT CGG CGC CGC CTT AAG AGG CGC TGC GAG GGC C | |
| HCV 2 | CTA GAG AGC GCA AGA CGC CCC GCG TCA CCG GCG GCG | |
| GBV B1 | GGA GAT CTC GTA GAC CGT AGC ACA TG | 428–448 |
| GBV B2 | GGG GAT CCC TAG TGG ACA CCG AAC CAA CCA GTA GCC CA | 842–868 |
| GBV B3 | GGG GAT CCT CAG ATC ACA CAA CCA GGC TCG TGT AGG | 1003–1029 |
| GBV B4 | GGG TAC TCT AGA GTG ATA GGC CTG GTC | 1618–1639 |
| GBV B5 | GBV CTA GAG AGC GCA AGA CGC CGC GGG TCA CCG GTG GCT CTC GCA ATC TTG G | |

[a]Nucleotide positions on the GBV-B viral genome (Genbank Accession No. NC001655) for the GBV-B primers Materials and Methods Construction of Plasmids Construction of plasmids pSFV/1-195 and pSFV/1-169 has been described previously (19). The codons for the proline residues in these constructs were mutated to encode alanine by insertion of an oligonucleotide (HCV1 in Table 1). This oligonucleotide was inserted between BspHI and BstX1 sites in construct pgHCV/□135-144 (19) to give plasmid pgHCV/1-195$_{(P \blacktriangleright A)}$; the BspHI site is not a natural site in the sequence for HCV strain Glasgow and was introduced during the construction of pgHCV/□135-144. To generate pSFV/1-195$_{(P \blacktriangleright A)}$ and pSFV/1-169$_{(P \blacktriangleright A)}$, a 502 bp fragment from pgHCV/1-195$_{(P \blacktriangleright A)}$, produced by cleavage by BglII and BstEII, was inserted into pSFV/1-195 and pSFV/1-169 digested with the same enzymes. A tagged version of HCV core was generated by firstly converting the nucleotide sequence in pg/1-195 that encodes amino acids 116 and 117 from TCG CGC to TCT AGA; this introduced a novel XbaI site into the HCV core-coding region without changing the encoded amino acids. An oligonucleotide (HCV2 in Table 1) that encoded the epitope tag (32) was introduced into the XbaI site to give plasmid pg/1-195tag. The tagged version of core was transferred as a BglII fragment from pg/1-195tag into Semliki Forest virus (SFV) expression vector pSFV1 (33) to give construct pSFV/1-195tag.

To express portions of the GBV-B polyprotein, relevant regions were amplified by PCR from a construct pGBB (30). pGBB contains the consensus sequence for an infectious molecular clone of GBV-B (30). Primers for PCR amplification were derived from the viral sequences in pGBB and were used in the following pairs to produce DNA fragments that encoded N-terminal regions of the GBV-B polyprotein: residues 1–141, GBV-B primers 1 and 2; residues 1–194, GBV-B primers 1 and 3; residues 1–398, GBV-B primers 1 and 4. Amplified fragments were introduced initially into plasmid pGEM1 and thereafter into pSFV1 by standard cloning techniques. To permit detection of GBV-B core, an epitope tag (32) was introduced into the coding region immediately following amino acid residue 85 (FIG. 6). This was accomplished by firstly introducing a novel XbaI site at nucleotide residue 695 by converting the sequence from TCT CGC to TCT AGA; this did not alter the encoded amino acid sequence. An oligonucleotide encoding the epitope tag (GBV-B5 in Table 1) was inserted between this XbaI site and a TfiI site (position 708 in the native GBV-B nucleotide sequence). The final SFV constructs that contained tagged versions of GBV-B core were termed pSFV/GB 1-141, pSFV/GB1-194 and pSFV/GB 1-398.

Maintenance of Tissue Culture Cells and Treatment with MG132

Baby hamster kidney (BHK) C13 cells were grown and maintained in Glasgow minimal Eagle's Medium supplemented with 10% new-born calf serum (CS), 4% tryptose phosphate broth, and 100 IU/ml penicillin/streptomycin (ETC10). To treat 1BHK cells with MG132 (supplied by Boston Biochem), cells were incubated for 5 h after electroporation at 37° C. and the media was replaced with fresh media containing the protease inhibitor at a final concentration of 2.5 µg/ml. Incubation was continued at 37° C. for a further 12 h before the cells were either harvested for Western blot analysis or fixed for indirect immunofluorescence studies.

Immunological Reagents

The monoclonal antibodies (MAb) used to detect HCV core protein (MAb JM122) and the epitope tag (MAb 9220) have been described previously (19 and 32 respectively).

1. In Vitro Transcription and Electroporation of SFV RNA into Cells

RNA was transcribed in vitro from recombinant pSFV constructs linearized with SpeI. BHK cells were electroporated with in vitro transcribed RNA as described previously (19, 36). Cells were incubated at 37° C. for 15 h and then harvested.

Preparation of Cell Extracts, Polyacrylamide Gel Electrophoresis and Western Blot Analysis Extracts were prepared and polyacrylamide gel electrophoresis performed as described previously (19, 36).

For Western blot analysis, proteins separated on polyacrylamide gels were transferred to nitrocellulose membrane. After blocking with 3% gelatin, 4 mM Tris-HCl, pH 7.4, 100 mM NaCl, membranes were incubated with antibodies (diluted to 1/500) in 1% gelatin, 4 mM Tris-HCl, pH 7.4, 100 mM NaCl, 0.05% Tween 20. After washing, bound antibody was detected using a horseradish peroxidase-conjugated secondary antibody followed by enhanced chemiluminescence (Amersham, UK).

Indirect Immunofluorescence and Staining of Lipids

Cells on 13 mm coverslips were fixed for 30 min in 4% paraformaldehyde, 0.1% Triton X-100 (prepared in phosphate-buffered saline) at 4° C. Following washing with phosphate-buffered saline (PBS) and blocking with PBS/CS (PBS containing 1% newborn calf serum), cells were incubated with primary antibody (diluted in PBS/CS at 1/200 for JM122 and 9220 antibodies) for 2 h at room temperature. Cells were washed extensively with PBS/CS and then incubated with conjugated secondary antibody (either antimouse or anti-rabbit IgG raised in goat) for 2 h at room temperature. Cells were washed extensively in solutions of PBS/CS followed by PBS. Staining of lipid droplets by oil red O was performed as described previously (19). Cells were rinsed finally with $H_2O$ before mounting on slides using Citifluor (Citifluor Ltd., UK). Samples were analyzed using a Zeiss LSM confocal microscope.

Computing

Sequences were aligned using the CLUSTAL W alignment program (37) and hydropathicity plots generated by ProtScale (38).

Results

A Domain in the HCV Core Protein that is Absent in Flavi- and Pestiviruses but Present in GBV-B Previously, it was proposed that the HCV core protein consisted of 3 domains and that the second of these domains was absent in related pesti- and flaviviruses (19, 39). Although there is a lack of sequence identity between viral sequences in the Flaviviridae, each of the capsid proteins in members of this virus family have a high content of basic amino acids (40). Therefore, the comparisons described here were based on the proportion of positively charged residues in predicted coding regions accompanied by hydropathicity plot studies. It was found that the mature capsid (C) protein of yellow fever virus (YF), a flavivirus, had a high proportion of basic residues (27%). In contrast, the signal peptide sequence that is removed from C protein upon maturation did not contain any basic amino acids. Up to amino acid 117 of the HCV core protein, 23% of residues were basic and this dropped to 7% between residues 118–173. Thus, the N-terminal 117 amino acids of HCV core have a similar character to those in the YF C protein but there are no sequences corresponding to the region between 118 and 173 of the HCV polypeptide. Analysis of the hydropathicity of the HCV core protein also revealed a highly hydrophilic region containing a similar segment of basic residues (RRRSR) between residues 113–117 (FIG. 6). The region between residues 118 and 173 is referred to as domain 2 (19, 39).

A closely related virus to HCV is GBV-B, a virus that was isolated from tamarins but whose natural host is not known. To date, the proteolytic events to generate the mature proteins of GBV-B have been assumed from comparison with HCV polypeptide processing (29). Comparing the putative GBV-B core sequence with that of HCV did not identify any stretches of similarity until residue 75 of GBV-B (FIG. 6). According to the sequence alignment, domain 1 for GBV-B core ended at residue 85 (corresponding to residue 117 in HCV core; FIG. 6) and thus, for this domain, the GBV-B sequence was shorter than that for HCV. The overall sequence identity (sequence homology) between these domains in HCV and GBV-B was about 22%. From residue 86 and up to residue 140 of GBV-B, sequence identity between the two viral sequences increased to 41% and apart from one additional residue in GBV-B, the sequences were colinear (FIG. 6). In HCV core, this segment is composed principally of domain 2 and indicated that sequences corresponding to this region are present in GBV-B. Sequence identity between the residues 140–156 for GBV-B and 174–191 for HCV (corresponding to the signal peptide sequences) was slightly lower at 38% and reduced further in the equivalent E1 sequences (approx. 25%). Distribution of basic residues in the putative GBV-B core protein revealed a high lysine/arginine content (21%) in the N-terminal region up to amino acid 85, a reduced percentage beyond this point (3.6% between amino acids 86–136) and no positively charged amino acids in the signal peptide sequence. This pattern of distribution corresponded to that present in HCV core. From these data, it was concluded that the putative GBV-B core protein shares the same domain arrangement as its counterpart in HCV.

Intracellular Localization of the GBV-B Core Protein

Previous studies on the intracellular localization of HCV core showed that the protein was directed to lipid droplets and the primary sequence determinants for this localization were present in domain 2 (19). Since the region of highest homology between the core proteins of GBV-B and HCV encompassed this domain, we expressed a N-terminal region of the GBV-B polyprotein using pSFV/GB1-398 in which the coding region extended beyond the predicted C-terminus of E1 to analyze the intracellular localization of GBV-B core. As immunological reagents against GBV-B proteins were not available, we placed a short epitope tag (32) at residue 85 to detect the protein. Placing this tag into the corresponding region of the HCV core protein did not affect its intracellular localization and the protein was present on lipid droplets. Indirect immunofluorescence of cells electroporated with RNA from pSFV/GB1-398 using an antibody, 9220, that recognizes the epitope tag revealed staining around lipid droplets stained with oil red O. Western blot analysis of cell extracts indicated that the size of core protein detected was approximately 17 kDa. This is consistent with a product of about 155 amino acids (comprising 143 amino acids of GBV-B and 12 amino acids of the epitope tag).

To further verify the intracellular localization of GBV-B core and the likely events involved in its maturation, two other constructs containing GBV-B sequences were examined. Firstly, a construct pSFV/GB1-141 that would correspond approximately in size to the product detected with pSFV/GB1-398. Analysis of cells expressing the tagged product produced by pSFV/GB1-141 again revealed localization of the protein around lipid droplets. The size of the protein made by pSFV/GB1-141 was only slightly smaller than that made by pSFV/GB1-398. Another construct that expressed the N-terminal 194 residues of GBV-B gave a major product that was identical in size to that produced by pSFV/GB1-398; a second minor band of about 20 kDa represented uncleaved protein. It was concluded that, in common with HCV core, the equivalent GBV-B protein is directed to lipid droplets in tissue culture cells and cleavage of the GBV-B polyprotein to produce the mature form of core is directed by cellular peptidases. Our studies on HCV core revealed that domain 2 contained the sequences essential for lipid droplet association. Based on our sequence comparisons, this domain is present also in the equivalent GBV-B protein. Hence, we propose that the essential sequences for association with lipid droplets reside within the corresponding region of GBV-B core.

Discussion

From previous analysis and data presented in this example, it was proposed that the HCV core protein consisted of three domains (19, 39). Domain 1 corresponded to the mature core protein of flaviviruses while no sequences equivalent to domain 2 were present in either pesti- or flaviviruses. Domain 3 contained the signal peptide sequence that directs the HCV E1 glycoprotein to the ER lumen. Here, the sequence comparisons were extended to include GBV-B, a virus that is the closest known related virus to HCV in terms of sequence identity (29). From comparisons of the two viral sequences, domain 2 in HCV core was found also in the corresponding GBV-B protein. Sequence identity between the predicted amino acid sequences of HCV and GBV-B in the region containing domain 2 was higher (approx. 41%) than that in the N- and C-terminal flanking regions. This degree of similarity would imply that these domains in HCV and GBV-B might perform similar functions. Extensive mutational analysis and immunolocalization studies of the HCV core protein showed that domain 2 contained the key elements for directing the protein to lipid droplets (19). The data presented in this example indicated that the core protein of GBV-B also could associate with these lipid storage structures. Thus, we conclude that a function of these domains is to direct the core protein of the two viruses to lipid storage organelles.

From the above evidence, it was concluded that the HCV and GBV-B core proteins have similar domain configurations. Based on our data (19 and this example), domain 2 in both proteins represented sequences that directed them to lipid droplets. Comparison with mammalian proteins that associate with these structures did not identify any region in such proteins with features similar to those in domain 2.

The HCV and GBV-B core proteins each contained two closely spaced proline residues within domain 2. Substitution of these prolines in HCV core abolished lipid droplet association. We have shown previously that removal of short sequence elements of domain 2 from HCV core prevented lipid droplet association (19). Based on these findings, we suggest that the HCV and GBV-B core may be members of a family of proteins that share similar sequence characteristics for targeting to lipid droplets.

To summarize this example, in mammalian tissue culture cells, the core protein of hepatitis C virus (HCV) is located at the surface of lipid droplets, which are cytoplasmic structures that store lipid. The critical amino acid sequences necessary for this localization are in a region of core protein that is absent in flavi- and pestiviruses, which are related to HCV. From sequence comparisons, this region in HCV core was present in the corresponding protein of GB virus-B (GBV-B), another virus whose genomic sequence has significant similarity (homology as defined herein) to HCV. Expression of the putative GBV-B core protein revealed that it also was directed to lipid droplets. Extending the comparisons to mammalian cellular proteins, there were no amino acid similarities with the domains for lipid droplet association in HCV core.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

GENERAL REFERENCES

1. Atschul et al., 1990, J Mol Biol: 403–410.
2. Altschul et al., 1994, Nature Genetics 6:119–129
3. Barba, G. et al., 1997. Proc. Natl. Acad. Sci. 94: 1200–1205
4. Cibelli, J. B. et al., 1998, Science 280; 1256–1258
5. Claverie & States (1993) Computers and Chemistry 17:191–201
6. Devereux et al, 1984, Nucleic Acids Research 12: 387
7. Engelman et al., 1986, Ann Rev, Biophys. Chem 15: 343
8. Freudenstein, C. et al., 1979, Experimental Cell Research 118; 277–294
9. Heid et al., 1998, Cell Tiss Res 294: 309–321
10. McLauchlan, J. et al., 1994, J. Gen Virol. 75; 2047–2052,
11. Moradpour, D. et al., 1996, Virology 222; 51–63
12. Moriya, K. et al., 1998, Nature Medicine 4; 1065–1067
13. Moriya, K. et al., 1997, J. Gen. Virol. 78; 1527–1531
14. Patton, S. and Huston, G. E., 1986, Lipids 21; 170–174
15. Schnieke, A. E. et al., 1997, Science 278; 2130–2133
16. Sola, I. et al., 1998, J. Virol. 72; 3762–3772
17. Wootton & Federhen, 1993, Computers and Chemistry 17: 149–163

REFERENCES FOR EXAMPLE 7

1. Murphy, D. J., and Vance, J. (1999) *Trends Biol. Sci.* 24, 109–115.
2. Zwytick, D., Athenstaedt, K., and Daum, G. (2000) *Biochim. Biophys Acta* 1469, 101–120.
3. Murphy, D. J. (2001) Prog. Lipid Res. 40,325–438.
4. Huang, A. H. C. (1996) *Plant Physiol.* 110, 1055–1061.
5. van Rooijen, G. J. H., and Moloney, M. M. (1995) *Plant Physiol.* 109, 1353–1361.
6. Abell, B. M., Holbrook, L. A., Abenes, M., Murphy, D. J., Hills, M. J., and Moloney, M. M. (1997) *Plant Cell* 9, 1481–1493.
7. Jiang, H. P., and Serrero, G. (1992) *Proc. Natl. Acad. Sci. U.S.A.* 89, 7856–7860.
8. Brasaemle, D. L., Barber, T., Wolins, N. E., Serrero, G., Blanchette-Mackie, E. J., and Londos, C. (1997) *J. Lipid Res.* 38, 2249–2263.
9. Greenberg, A. S., Egan, J. J., Wek, S. A., Garty, N. B., Blanchette-Mackie, E. J., and Londos, C. (1991) *J. Biol. Chem.* 266; 11341–11346.
10. Greenberg, A. S., Egan, J. J., Wek, S. A., Moos, M. C. Jr., Londos, C., and Kimmel, A. R. (1993) *Proc. Natl. Acad. Sci. U.S.A.* 90, 12035–12039.
11. Londos, C., Brasaemle, D. L., Schultz, C. J., Segrest, J. P., and Kimmel, A. R. (1999) *Cell Develop. Biol.* 10, 51–58.

12. Heid, H. W., Moll, R., Schwetlick, I., Rackwitz, H. R., and Keenan, T. W. (1998) *Cell Tissue Res.* 294, 309–321.
13. Wang, X. K., Reape, T. J., Li, X., Rayner, K., Webb, C. L., Burnand, K. G., and Lysko, P. G. (1999) *FEBS Lett.* 462, 145–150.
14. Rae, F. K., Stephenson, S. A., Nicol, D. L., and Clements, J. A. (2000) *Int. J. Cancer* 88, 726–732.
15. Blanchette-Mackie, E. J., Dwyer, N. K., Barber, T., Coxey, R. A., Takeda, T., Rondinone, C. M., Theodorakis, J. L., Greenberg, A. S., and Londos, C. (1995) *J. Lipid Res.* 36, 1211–1226.
16. Servetnick, D. A., Brasaemle, D. L., Gruia-Gray, J., Kimmel, A. R., Wolff, J., and Londos, C. (1995) *J. Biol. Chem.* 270, 16970–16973.
17. Moradpour, D., Englert, C., Wakita, T., and Wands, J. R. (1996) *Virology* 222, 51–63.
18. Barba, G., Harper, F., Harada, T., Kohara, M., Goulinet, S., Matsuura, Y., Eder, G., Schaff, Zs., Chapman, M. J., Miyamura, T., and Brechot, C. (1997) *Proc. Natl. Acad. Sci. U.S.A.* 94, 1200–1205.
19. Hope, R. G., and McLauchlan, J. (2000) *J. Gen. Virol.* 81, 1913–1925
20. Baumert, T. F., Ito, S., Wong, D. T., and Liang, T. J. (1998) *J. Virol.* 72, 3827–3836.
21. Rice, C. M. (1996) in *Fields Virology* (Fields, B. N., Knipe, D. M., Howley, P. M. et al., eds) 3$^{rd}$ ed. Vol 1, pp.931–960, Lippincott-Raven Publishers, Philadelphia, Pa.
22. Hijikita, M., Kato, N., Ootsuyuma, Y., Nakagawa, M., and Shimotohno, K. (1991) *Proc. Natl. Acad. Sci. U.S.A.* 88, 5547–5551.
23. Grakoui, A., Wychowski, C., Lin, C., Feinstone, S. M., and Rice, C. M. (1993) *J. Virol.* 67, 1385–1395.
24. Santolini, E., Migliaccio, G., and La Monica, N. (1994) *J. Virol.* 68, 3631–3641.
25. Lo, S.-Y., Masiarz, F., Hwang, S. B., Lai, M. M. C., and Ou, J.-H. (1995) *Virology* 213, 455–461.
26. Hussy, P., Langen, H., Mous, J., and Jacobsen, H. (1996) *Virology* 224, 93–104.
27. Moriya, K., Yotsuyanagi, H., Shintani, Y., Fujie, H., Ishibashi, K., Matsuura, Y., Miyamura, T., and Koike, K. (1997) *J. Gen. Virol.* 78, 1527–1531.
28. Sabile, A., Perlemuter, G., Bono, F., Kohara, K., DeMaugre, F., Kohara, M., Matsuura, Y., Miyamura, T., Brechot, C., and Barba, G. (1999) *Hepatology* 30, 1064–1076.
29. Muerhoff, A. S., Leary, T. P., Simons, J. N., Pilot-Matias, T. J., Dawson, G. J., Erker, J. C., Chalmers, M. L., Schlauder, G. G., Desai, S. M., and Mushahwar, I. K. (1995) *J. Virol.* 69, 5621–5630.
30. Beames, B., Chavez, D., Guerra, B., Notvall, L., Brasky, K. M. and Lanford, R. E. (2000) *J. Virol.* 74; 11764–11772.
31. Bukh, J., Apgar, C. L., and Yanagi, M. (1999) *Virology* 262, 470–478.
32. McLauchlan, J., Liefkens, K., and Stow, N. D. (1994) *J. Gen. Virol.* 75, 2047–2052.
33. Liljestrom, P., and Garoff, H. (1991) *Bio-Technology* 9, 1356–1361.
34. Keddie, J. S., Hubner, G., Slocombe, S. P., Jarvis, R. P., Cummins, I., Edwards, E. W., Shaw, C. H., and Murphy, D. J. (1992) *Plant Mol. Biol.* 19, 443–453.
35. Sarmiento, C., Ross, J. H. E., Herman, E., and Murphy, D. J. (1997) *Plant Journal* 11, 783–796.
36. Patel, J., Patel, A. H., and McLauchlan, J. (1999) *J. Gen. Virol.* 80, 1681–1690.
37. Thompson, J. D., Higgins, D. G., and Gibson, T. J. (1994) *Nucl. Acids Res.* 22, 4673–4680.
38. Kyte, J., and Doolittle, R. F. (1982) *J. Mol. Biol.* 157, 105–132.
39. McLauchlan, J. (2000) *J. Viral Hepatitis* 7, 2–14.
40. Mandl, C. W., Heinz, F. X., and Kunz, C. (1988) *Virology* 166, 197–205.
41. Amberg, S. M., Nestorowicz, A., McCourt, D. W., and Rice C. M. (1994) *J. Virol.* 68, 3794–3802.
42. Amberg, S. M. and Rice, C. M. (1999) *J. Virol.* 73, 8083–8094.
43. Nielsen, H., Engelbrecht, J., Brunak, S., and von Heijne, G. (1997) *Protein Eng.* 10, 1–6.
44. Ting, J. T. L., Balsamo, R. A., Ratnayake, C., and Huang, A. H. C. (1997) *J. Biol. Chem.* 272, 3699–3706.
45. Chen, J. C. F., Tsai, C. C. Y., and Tzen, J. T. C. (1999) *Plant Cell Physiol.* 40, 1079–1086.
46. Naested, H., Frandsen, G. I., Jauh, G-Y., Hernandez-Pinzon, I., Nielsen, H. B., Murphy, D. J., Rogers, J. C., and Mundy, J. (2000) *Plant Mol. Biol.* 44, 463–476.
47. Lacey, D. J., Wellner, N., Beaudoin, F., Napier, J. A., and Shewry, P. R. (1998) *Biochem. J.* 334, 469–477.
48. Fujimoto, T., Kogo, H., Ishiguro, K., Tauchi, K., and Nomura, R. (2001) *J. Cell Biol.* 152, 1079–1085.
49. Ostermeyer, A. G., Paci, J. M., Zeng, Y., Lublin, D. M., Munro, S., and Brown, D. A. (2001) *J. Cell Biol.* 152, 1071–1078.
50. Pol, A., Luetterforst, R., Lindsay, M., Heino, S., Ikonen, E., and Parton, R. G. (2001) *J. Cell Biol.* 152, 1057–1070.
51. Li, M., Smith, L. J., Clark, D. C., Wilson, R., and Murphy, D. J. (1992) *J. Biol. Chem.* 267, 8245–8253.

What is claimed is:

1. A polynucleotide encoding a fusion protein, wherein said fusion protein comprises a lipid globule targeting sequence linked to a protein of interest (POI), wherein the targeting sequence comprises a hepatitis C virus (HCV) core protein or fragment or homologue of a hepatitis C virus (HCV) core protein.

2. A polynucleotide according to claim 1 wherein the fragment comprises amino acids from 125 to 144 and/or 161 to 166 of the HCV core protein together with a hydrophilic sequence.

3. A polynucleotide according to claim 1 wherein the POI comprises at least one epitope.

4. A polynucleotide according to claim 3 wherein the POI is a viral or bacterial protein or fragment thereof.

5. A polynucleotide according to claim 4 wherein the POI is an HCV antigen.

6. A polynucleotide according to claim 1 operably linked to a control sequence permitting expression of the protein in a suitable host cell.

7. A polynucleotide according to claim 6 wherein the host cell is an adipocyte.

8. A polynucleotide according to claim 7 wherein the host cell is a milk-secreting cell.

9. A polynucleotide according to claim 8 wherein said targeting sequence comprises a hepatitis C virus (HCV) core protein homologue of a fragment thereof, wherein said homologue is GB virus-B core protein or a fragment thereof.

10. A nucleic acid vector comprising a polynucleotide according to claim 1.

11. A nucleic acid vector according to claim 10 wherein said polynucleotide is operably linked to a polylinker cloning site.

12. A host cell comprising a polynucleotide according to claim 1.

13. A host cell comprising a nucleic acid vector according to claim 10.

14. A method comprising expressing a polynucleotide according to claim 1.

15. A method according to claim 14 wherein the expressed product is isolated.

16. A fusion protein comprising a lipid globule targeting sequence linked to a protein of interest (POI) wherein the targeting sequence comprises a hepatitis C virus (HCV) core protein or homologue or fragment of a hepatitis C virus (HCV) core protein or a fragment of said hepatitis C virus (HCV) core protein homologue.

* * * * *

SEQUENCE LISTING

<160> NUMBER OF SEQ ID NOS: 18

<210> SEQ ID NO 1
<211> LENGTH: 630
<212> TYPE: DNA
<213> ORGANISM: Hepatitis C Virus
<220> FEATURE:
<221> NAME/KEY: CDS
<222> LOCATION: (43)...(630)

<400> SEQUENCE: 1
ggtgcttgcg agtgccccgg gaggtctcgt agaccgtgca cc atg agc acg aat    54
                                              Met Ser Thr Asn
                                              1

```
cct aaa cct caa aga aaa acc aaa cgt aac acc aac cgt cgc cca cag      102
Pro Lys Pro Gln Arg Lys Thr Lys Arg Asn Thr Asn Arg Arg Pro Gln
 5              10                  15                  20 gac gtt aag ttc ccg ggt ggc ggt cag atc gtt ggt gga gtt tac ttg      150
Asp Val Lys Phe Pro Gly Gly Gly Gln Ile Val Gly Gly Val Tyr Leu
                25                  30                  35 ttg ccg cgc agg ggc cct aga ttg ggt gtg cgc gcg acg agg aag act      198
Leu Pro Arg Arg Gly Pro Arg Leu Gly Val Arg Ala Thr Arg Lys Thr
        40                  45                  50 tcc gag cgg tcg caa cct cga ggt aga cgt cag cct atc ccc aag gca      246
Ser Glu Arg Ser Gln Pro Arg Gly Arg Arg Gln Pro Ile Pro Lys Ala
            55                  60                  65 cgt cgg ccc aag ggc agg aac tgg gct cag ccc ggg tat cct tgg ccc      294
Arg Arg Pro Lys Gly Arg Asn Trp Ala Gln Pro Gly Tyr Pro Trp Pro
    70                  75                  80 ctc tat ggc aat gag ggt tgc ggg tgg gcg gga tgg ctc ctg tcc ccc      342
Leu Tyr Gly Asn Glu Gly Cys Gly Trp Ala Gly Trp Leu Leu Ser Pro
85                  90                  95                 100 agt ggc tct cgg cct agt tgg ggc ccc aac gac ccc cga cgt agg tcg      390
Ser Gly Ser Arg Pro Ser Trp Gly Pro Asn Asp Pro Arg Arg Arg Ser
                105                 110                 115 cgc aat ttg ggt aag gtc atc gat acc ctt acg tgc ggc ttc gtc gat      438
Arg Asn Leu Gly Lys Val Ile Asp Thr Leu Thr Cys Gly Phe Val Asp
        120                 125                 130 ctc atg ggg tac ata ccg ctc gtc ggc gcc cct ctt aga ggc gct gcc      486
Leu Met Gly Tyr Ile Pro Leu Val Gly Ala Pro Leu Arg Gly Ala Ala
            135                 140                 145 agg gcc ctg gcg cat ggc gtc cgg gtt ctg gaa gac ggt gtg aac tat      534
Arg Ala Leu Ala His Gly Val Arg Val Leu Glu Asp Gly Val Asn Tyr
    150                 155                 160 gca aca ggt aac ctt cct ggt tgc tct ttc tct atc ttc ctt ctg gcc      582
Ala Thr Gly Asn Leu Pro Gly Cys Ser Phe Ser Ile Phe Leu Leu Ala
165                 170                 175                 180 ctg ctc tct tgc ctg act gtg ccc gct tca gcc tac caa gtg cgc aac      630
Leu Leu Ser Cys Leu Thr Val Pro Ala Ser Ala Tyr Gln Val Arg Asn
                185                 190                 195

<210> SEQ ID NO 2
<211> LENGTH: 60
<212> TYPE: DNA
<213> ORGANISM: Hepatitis C Virus
<220> FEATURE:
<221> NAME/KEY: CDS
<222> LOCATION: (1)...(60)
<223> OTHER INFORMATION: Corresponds to amino acids 125-144 of the HCV
      Core protein sequence

<400> SEQUENCE: 2 acc ctt acg tgc ggc ttc gtc gat ctc atg ggg tac ata ccg ctc gtc       48
Thr Leu Thr Cys Gly Phe Val Asp Leu Met Gly Tyr Ile Pro Leu Val
 1               5                  10                  15 ggc gcc cct ctt                                                       60
Gly Ala Pro Leu
            20

<210> SEQ ID NO 3
<211> LENGTH: 18
<212> TYPE: DNA
<213> ORGANISM: Hepatitis C Virus
<220> FEATURE:
<221> NAME/KEY: CDS
<222> LOCATION: (1)...(18)
<223> OTHER INFORMATION: Corresponds to Hepatitis C Virus core protein
``` amino acids 161-166

<400> SEQUENCE: 3 ggt gtg aac tat gca aca                                                    18
Gly Val Asn Tyr Ala Thr
  1               5

<210> SEQ ID NO 4
<211> LENGTH: 31
<212> TYPE: PRT
<213> ORGANISM: Artificial Sequence
<220> FEATURE:
<223> OTHER INFORMATION: A branched peptide containing residues 5-27 or
      the core protein ecoded by HCV strain Glasgow.  Sites
      1 and 12 are degenerate with site 1 being Ala or
      Pro and site 12 being Ile or Asn

<400> SEQUENCE: 4

Ala Lys Pro Gln Arg Lys Thr Lys Arg Asn Thr Ile Arg Arg Pro Gln
  1               5                  10                  15

Asp Val Lys Phe Pro Gly Gly Lys Lys Lys Lys Lys Lys Ala
             20                  25                  30

<210> SEQ ID NO 5
<211> LENGTH: 11
<212> TYPE: DNA
<213> ORGANISM: Artificial Sequence
<220> FEATURE:
<223> OTHER INFORMATION: Oligonucleotide used to produce the Hepatitis
      C virus core deletion plasmids

<400> SEQUENCE: 5
gctgagatct a                                                               11

<210> SEQ ID NO 6
<211> LENGTH: 29
<212> TYPE: DNA
<213> ORGANISM: Artificial Sequence
<220> FEATURE:
<223> OTHER INFORMATION: Oligonucleotide used to produce the Hepatitis
      C virus core deletion plasmids

<400> SEQUENCE: 6
gtaaccttcc tggttgctct tgagatcta                                            29

<210> SEQ ID NO 7
<211> LENGTH: 17
<212> TYPE: DNA
<213> ORGANISM: Artificial Sequence
<220> FEATURE:
<223> OTHER INFORMATION: Oligonucleotide used to produce the Hepatitis
      C virus core deletion plasmids

<400> SEQUENCE: 7
gtaacctttg agatcta                                                         17

<210> SEQ ID NO 8
<211> LENGTH: 18
<212> TYPE: DNA
<213> ORGANISM: Artificial Sequence
<220> FEATURE:
<223> OTHER INFORMATION: Oligonucleotide used to produce the Hepatitis
      C virus core deletion plasmids

<400> SEQUENCE: 8
ctggcgcatt gagatcta                                                        18

<210> SEQ ID NO 9
<211> LENGTH: 28
<212> TYPE: DNA
<213> ORGANISM: Artificial Sequence
<220> FEATURE:
<223> OTHER INFORMATION: Oligonucleotide used to produce the Hepatitis
      C virus core deletion plasmids

<400> SEQUENCE: 9
ctggcccatg gtgttaacta tgcaacag                                      28

<210> SEQ ID NO 10
<211> LENGTH: 31
<212> TYPE: DNA
<213> ORGANISM: Artificial Sequence
<220> FEATURE:
<223> OTHER INFORMATION: Oligonucleotide used to produce the Hepatitis
      C virus core deletion plasmids

<400> SEQUENCE: 10
ctggcccatg gcgtccgggt tctggaagac g                                  31

<210> SEQ ID NO 11
<211> LENGTH: 32
<212> TYPE: DNA
<213> ORGANISM: Artificial Sequence
<220> FEATURE:
<223> OTHER INFORMATION: Oligonucleotide used to produce the Hepatitis
      C virus core deletion plasmids

<400> SEQUENCE: 11
gaggcgctgc cagggccctg gcgtgagatc ta                                 32

<210> SEQ ID NO 12
<211> LENGTH: 52
<212> TYPE: DNA
<213> ORGANISM: Artificial Sequence
<220> FEATURE:
<223> OTHER INFORMATION: Oligonucleotide used to generate constructs,
      identified as HCV1

<400> SEQUENCE: 12 catgggtac atagcgctcg tcggcgccgc cttaagaggc gctgcagggg cc             52

<210> SEQ ID NO 13
<211> LENGTH: 36
<212> TYPE: DNA
<213> ORGANISM: Artificial Sequence
<220> FEATURE:
<223> OTHER INFORMATION: Oligonucleotide used to generate constructs,
      identified as HCV2

<400> SEQUENCE: 13
ctagagagcg caagacgccc cgcgtcaccg gcggcg                             36

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide used to generate constructs,
      identified as GBV-B1

<400> SEQUENCE: 14
ggagatctcg tagaccgtag cacatg                                        26

<210> SEQ ID NO 15

-continued

```
<211> LENGTH: 38
<212> TYPE: DNA
<213> ORGANISM: Artificial Sequence
<220> FEATURE:
<223> OTHER INFORMATION: Oligonucleotide used to generate constructs,
      identified as GBV-B2

<400> SEQUENCE: 15
ggggatccct agtggacacc gaaccaacca gtagccca                        38

<210> SEQ ID NO 16
<211> LENGTH: 36
<212> TYPE: DNA
<213> ORGANISM: Artificial Sequence
<220> FEATURE:
<223> OTHER INFORMATION: Oligonucleotide used to generate constructs,
      identified as GBV-B3

<400> SEQUENCE: 16
ggggatcctc agatcacaca accaggctcg tgtagg                          36

<210> SEQ ID NO 17
<211> LENGTH: 27
<212> TYPE: DNA
<213> ORGANISM: Artificial Sequence
<220> FEATURE:
<223> OTHER INFORMATION: Oligonucleotide used to generate constructs,
      identified as GBV-B4

<400> SEQUENCE: 17
gggtactcta gagtgatagg cctggtc                                    27

<210> SEQ ID NO 18
<211> LENGTH: 49
<212> TYPE: DNA
<213> ORGANISM: Artificial Sequence
<220> FEATURE:
<223> OTHER INFORMATION: Oligonucleotide used to generate constructs,
      identified as GBV-B5

<400> SEQUENCE: 18
ctagagagcg caagacgccg cgggtcaccg gtggctctcg caatcttgg            49
```